United States Patent
Newton et al.

(10) Patent No.: US 11,628,086 B2
(45) Date of Patent: Apr. 18, 2023

(54) APPARATUS AND METHODS FOR RECEIVING DISCHARGED URINE

(71) Applicant: PureWick Corporation, El Cajon, CA (US)

(72) Inventors: Camille R. Newton, Bonsall, CA (US); Raymond J. Newton, Bonsall, CA (US)

(73) Assignee: PUREWICK CORPORATION, El Cajon, CA (US)

( * ) Notice: Subject to any disclaimer, the term of this patent is extended or adjusted under 35 U.S.C. 154(b) by 0 days.

(21) Appl. No.: 16/899,956

(22) Filed: Jun. 12, 2020

(65) Prior Publication Data

US 2020/0306075 A1 Oct. 1, 2020

Related U.S. Application Data

(63) Continuation of application No. 15/612,325, filed on Jun. 2, 2017, now Pat. No. 10,973,678, which is a
(Continued)

(51) Int. Cl.
*A61F 5/453* (2006.01)
*A61M 1/00* (2006.01)

(52) U.S. Cl.
CPC .............. *A61F 5/453* (2013.01); *A61M 1/71* (2021.05); *A61M 1/88* (2021.05);
(Continued)

(58) Field of Classification Search
CPC ............ A61F 5/453; A61M 1/0023; A61M 2202/0496; A61M 2210/1096; A61M 2210/167
(Continued)

(56) References Cited

U.S. PATENT DOCUMENTS 670,602 A 3/1901 Baker
1,032,841 A 7/1912 Koenig
(Continued)

FOREIGN PATENT DOCUMENTS

CA 2165286 C 9/1999
CA 2354132 A1 6/2000
(Continued)

OTHER PUBLICATIONS

US 9,908,683 B2, 03/2018, Sandhausen et al. (withdrawn)
(Continued)

*Primary Examiner* — Andrew J Mensh
(74) *Attorney, Agent, or Firm* — Dorsey & Whitney LLP

(57) ABSTRACT

A system suitable for collecting and transporting urine away from the body of a person or animal may include an assembly having a fluid impermeable casing, a fluid permeable membrane, and a fluid permeable support. A reservoir is defined by the fluid permeable support. The fluid permeable membrane can define a cavity. The casing can define an opening such that the cavity is accessible via the opening. The assembly can also include an outlet in fluidic communication with the reservoir. The assembly can be arranged such that a user's penis can be disposed through the opening with the urethral opening disposed within the cavity and such that a fluid can flow into the body from the urethral opening of the user's penis, collect in the reservoir, and flow out of the outlet.

17 Claims, 6 Drawing Sheets

Related U.S. Application Data continuation-in-part of application No. 15/238,427, filed on Aug. 16, 2016, now Pat. No. 10,376,407, which is a continuation-in-part of application No. 15/221,106, filed on Jul. 27, 2016, now Pat. No. 10,376,406.

(52) U.S. Cl.
CPC ............... *A61M 2202/0496* (2013.01); *A61M 2210/1096* (2013.01); *A61M 2210/167* (2013.01)

(58) Field of Classification Search
USPC .......................................................... 604/349
See application file for complete search history.

(56) References Cited

U.S. PATENT DOCUMENTS

| | | |
|---|---|---|
| 1,742,080 A | 12/1929 | Jones |
| 1,979,899 A | 11/1934 | Obrien et al. |
| 2,326,881 A | 8/1943 | Packer |
| 2,613,670 A | 10/1952 | Edward |
| 2,644,234 A | 7/1953 | Earl |
| 2,859,786 A | 11/1958 | Tupper |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,198,994 A | 8/1965 | Hildebrandt et al. |
| 3,221,742 A | 12/1965 | Egon |
| 3,312,981 A | 4/1967 | Mcguire et al. |
| 3,349,768 A * | 10/1967 | Keane ................... A61F 5/455 604/347 |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,699,815 A | 10/1972 | Holbrook |
| 3,726,277 A | 4/1973 | Hirschman |
| 3,757,355 A | 9/1973 | Allen et al. |
| 3,843,016 A | 10/1974 | Bornhorst et al. |
| 3,863,798 A | 2/1975 | Kurihara et al. |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,553,968 A | 11/1985 | Komis |
| 4,581,026 A | 4/1986 | Schneider |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,681,570 A | 7/1987 | Dalton |
| 4,692,160 A | 9/1987 | Nussbaumer |
| 4,707,864 A | 11/1987 | Ikematsu et al. |
| 4,713,066 A | 12/1987 | Komis |
| 4,747,166 A * | 5/1988 | Kuntz ..................... A61F 5/455 4/144.1 |
| 4,752,944 A | 6/1988 | Conrads et al. |
| 4,769,215 A | 9/1988 | Ehrenkranz |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,799,928 A | 1/1989 | Crowley |
| 4,804,377 A | 2/1989 | Hanifl et al. |
| 4,812,053 A | 3/1989 | Bhattacharjee |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,882,794 A | 11/1989 | Stewart |
| 4,883,465 A | 11/1989 | Brennan |
| 4,886,508 A | 12/1989 | Washington |
| 4,886,509 A | 12/1989 | Mattsson |
| 4,889,533 A | 12/1989 | Beecher |
| 4,903,254 A | 2/1990 | Haas |
| 4,905,692 A | 3/1990 | More |
| 4,955,922 A | 9/1990 | Terauchi |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |
| 5,071,347 A | 12/1991 | Mcguire |
| 5,084,037 A | 1/1992 | Barnett |
| 5,100,396 A | 3/1992 | Zamierowski |
| 5,147,301 A | 9/1992 | Ruvio |
| 5,195,997 A | 3/1993 | Carns |
| 5,203,699 A | 4/1993 | Mcguire |
| 5,244,458 A | 9/1993 | Takasu |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,318,550 A | 6/1994 | Cermak et al. |
| 5,382,244 A | 1/1995 | Telang |
| 5,423,784 A | 6/1995 | Metz |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |

(56) References Cited

U.S. PATENT DOCUMENTS

| | | |
|---|---|---|
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,972,505 A | 10/1999 | Phillips et al. |
| 6,015,627 A | 1/2000 | Hirafune et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,263,887 B1 | 7/2001 | Dunn |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,406,463 B1 | 6/2002 | Brown |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,512,301 B1 | 1/2003 | Palanisamy |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,586,583 B1 | 7/2003 | Vierling, Jr. et al. |
| 6,592,560 B2 * | 7/2003 | Snyder .................. A61F 5/443 604/331 |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 * | 2/2007 | Trabold .................. A61F 5/455 4/144.1 |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |

(56) References Cited

U.S. PATENT DOCUMENTS

| | | |
|---|---|---|
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| D789,522 S | 6/2017 | Burgess et al. |
| 9,687,849 B2 | 6/2017 | Bruno et al. |
| 9,694,949 B2 | 7/2017 | Hendricks et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| D901,214 S | 11/2020 | Hu |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,027,900 B2 | 6/2021 | Liu |
| 11,045,346 B2 | 6/2021 | Argent et al. |
| D928,946 S | 8/2021 | Sanchez et al. |
| 11,179,506 B2 | 11/2021 | Barr et al. |
| 11,226,376 B2 | 1/2022 | Yamauchi et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1* | 2/2002 | Grundke ............... A61F 5/455 604/327 |
| 2002/0087131 A1 | 7/2002 | Wolff et al. |
| 2002/0189992 A1 | 12/2002 | Schmidt et al. |
| 2003/0004436 A1 | 1/2003 | Schmidt et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1* | 10/2003 | Harvie ................. A61F 5/453 604/355 |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0176731 A1 | 9/2004 | Cheng et al. |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0070861 A1* | 3/2005 | Okabe .................. A61F 5/455 604/327 |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0111648 A1 | 5/2006 | Vermaak |
| 2006/0155214 A1 | 7/2006 | Wightman |
| 2006/0200102 A1 | 9/2006 | Cooper |
| 2006/0229576 A1 | 10/2006 | Conway et al. |

(56) References Cited

U.S. PATENT DOCUMENTS

| | | |
|---|---|---|
| 2006/0231648 A1 | 10/2006 | Male et al. |
| 2006/0235359 A1 | 10/2006 | Marland |
| 2007/0006368 A1 | 1/2007 | Key et al. |
| 2007/0038194 A1 | 2/2007 | Wada et al. |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225666 A1 | 9/2007 | Otto |
| 2007/0225668 A1 | 9/2007 | Otto |
| 2007/0266486 A1 | 11/2007 | Ramirez |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1* | 11/2008 | Van Den Heuvel .... A61F 5/455 604/327 |
| 2009/0025717 A1 | 1/2009 | Pinel |
| 2009/0056003 A1 | 3/2009 | Ivie et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0137273 A1 | 6/2011 | Muellejans et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0240648 A1 | 10/2011 | Tucker |
| 2011/0265889 A1 | 11/2011 | Tanaka et al. |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0031774 A1 | 1/2014 | Bengtson |
| 2014/0157499 A1 | 6/2014 | Suzuki et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0359660 A1 | 12/2015 | Harvie |
| 2015/0366699 A1 | 12/2015 | Nelson |
| 2016/0029998 A1 | 2/2016 | Brister et al. |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0278662 A1 | 9/2016 | Brister et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0200101 A1 | 7/2018 | Su |
| 2018/0228642 A1 | 8/2018 | Davis et al. |
| 2019/0021899 A1 | 1/2019 | Viet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0282391 A1 | 9/2019 | Johannes et al. |
| 2019/0314189 A1 | 10/2019 | Acosta |

(56) References Cited

U.S. PATENT DOCUMENTS

| | | |
|---|---|---|
| 2019/0314190 A1 | 10/2019 | Sanchez et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0255189 A1 | 8/2020 | Liu |
| 2020/0276046 A1 | 9/2020 | Staali et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0385179 A1 | 12/2020 | Mccourt |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0121318 A1 | 4/2021 | Pinlac |
| 2021/0137724 A1 | 5/2021 | Ecklund et al. |
| 2021/0154055 A1 | 5/2021 | Villarreal |
| 2021/0170079 A1 | 6/2021 | Radl et al. |
| 2021/0220162 A1 | 7/2021 | Jamison |
| 2021/0220163 A1 | 7/2021 | Mayrand |
| 2021/0229877 A1 | 7/2021 | Ragias et al. |
| 2021/0267787 A1 | 9/2021 | Nazemi |
| 2021/0386925 A1 | 12/2021 | Hartwell et al. |
| 2022/0023091 A1 | 1/2022 | Ecklund et al. |
| 2022/0066825 A1 | 3/2022 | Saraf et al. |
| 2022/0248836 A1 | 8/2022 | Cagle et al. |

FOREIGN PATENT DOCUMENTS

| | | |
|---|---|---|
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 101262836 A | 9/2008 |
| CN | 102159159 A | 8/2011 |
| CN | 202184840 U | 4/2012 |
| CN | 103717180 A | 4/2014 |
| CN | 204562697 U | 8/2015 |
| CN | 105451693 A | 3/2016 |
| CN | 205849719 U | 1/2017 |
| CN | 107847384 A | 3/2018 |
| CN | 107920912 A | 4/2018 |
| CN | 209285902 U | 8/2019 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 19619597 A1 | 11/1997 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3752110 B1 | 3/2022 |
| EP | 4025163 A1 | 7/2022 |
| GB | 1011517 A | 12/1965 |
| GB | 1467144 A | 3/1977 |
| GB | 2106395 A | 4/1983 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2507318 A | 4/2014 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S63107780 U | 7/1988 |
| JP | H0267530 A | 3/1990 |
| JP | H02103871 A | 4/1990 |
| JP | H02131422 A | 5/1990 |
| JP | H0460220 A | 2/1992 |
| JP | H05123349 A | 5/1993 |
| JP | H1040141 A | 2/1998 |
| JP | H11113946 A | 4/1999 |
| JP | H11290365 A | 10/1999 |
| JP | 2000185068 A | 7/2000 |
| JP | 3087938 B2 | 9/2000 |
| JP | 2001054531 A | 2/2001 |
| JP | 2001070331 A | 3/2001 |
| JP | 2001276107 A | 10/2001 |
| JP | 2001276108 A | 10/2001 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 2006026108 A | 2/2006 |
| JP | 3123547 B2 | 6/2006 |
| JP | 2006204868 A | 8/2006 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011224070 A | 11/2011 |
| JP | 2012523869 A | 10/2012 |
| JP | 2015092945 A | 5/2015 |
| JP | 3198994 B2 | 7/2015 |
| JP | 2019525811 A | 9/2019 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |

(56) References Cited

FOREIGN PATENT DOCUMENTS

| | | |
|---|---|---|
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017152198 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021034886 A1 | 2/2021 |
| WO | 2021041123 A1 | 3/2021 |
| WO | 2021094352 A1 | 5/2021 |
| WO | 2021155206 A1 | 8/2021 |
| WO | 2021173436 A1 | 9/2021 |
| WO | 2021207621 A1 | 10/2021 |
| WO | 2021257202 A1 | 12/2021 |
| WO | 2022006256 A1 | 1/2022 |

(56) References Cited

FOREIGN PATENT DOCUMENTS

WO 2022140545 A1 6/2022
WO 2022150360 A1 7/2022

OTHER PUBLICATIONS

Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
AMXDmax In-Flight Bladder Relief; Omni Medical 2015; Omni Medical Systems, Inc.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 29/624,661 dated Feb. 18, 2020.
International Search Report and Written Opinion for International Application No. PCT/US2017/043025 dated Oct. 18, 2017.
International Search Report and Written Opinion for International Application No. PCT/US2018/015968 dated Apr. 6, 2018.
International Search Report and Written Opinion for International Patent Application No. PCT/US16/49274, dated Dec. 1, 2016.
International Search Report and Written Opinion from International Application No. PCT/US2017/035625 dated Aug. 15, 2017.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Non-Final Office Action for U.S. Appl. No. 14/722,613 dated Jun. 13, 2019.
Non-Final Office Action for U.S. Appl. No. 14/947,759, dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Jun. 12, 2018.
Non-Final Office Action for U.S. Appl. No. 15/171,968 dated Aug. 20, 2019.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 29/624,661 dated Jul. 18, 2019.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 29/624,661 dated May 14, 2020.
U.S. Appl. No. 15/171,968, filed Jun. 2, 2016.
U.S. Appl. No. 15/221,106, filed Jul. 27, 2016.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
Defendant and Counterclaim Plaintiff Sage Products, LLC'S Answer, Defenses, and Counterclaims To Plaintiff'S Amended Complaint, Nov. 1, 2019.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Step by Step How Ur24 WorksHome", http://medicalpatentur24.com, last accessed Dec. 6, 2017, Aug. 30, 2017, 4 pages.

(56) References Cited

OTHER PUBLICATIONS

Parmar, "10 Finalists Chosen for Dare-to-Dream Medtech Design Challenge (PureWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Final Office Action for U.S. Appl. No. 14/952,591 dated Nov. 27, 2020.
Final Office Action for U.S. Appl. No. 15/612,325 dated Sep. 17, 2020.
International Search Report and Written Opinion from International Application No. PCT/US2020/023572 dated Jul. 6, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
Issue Notification for U.S. Appl. No. 15/171,968 dated Mar. 3, 2021.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 17/088,272 dated Jan. 25, 2021.
Non-Final Office Action for U.S. Appl. No. 29/694,002 dated Jun. 24, 2020.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 29/624,661 dated Jul. 10, 2020.
Notice of Allowance for U.S. Appl. No. 29/624,661 dated Sep. 29, 2020.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 dated Mar. 3, 2021.
U.S. Appl. No. 15/260,103, filed Sep. 8, 2016.
U.S. Appl. No. 15/611,587, filed Jun. 1, 2017.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 29/741,751, filed Jul. 15, 2020.
U.S. Appl. No. 62/853,889, filed May 29, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/889,149, filed Aug. 20, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,210, filed Mar. 10, 2021.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.

(56) References Cited

OTHER PUBLICATIONS

"AMXD Control Starter Kit Brochure", https://www.omnimedicalsys.com/index.php?page=products, Omni Medical, 8 pages.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Sachtman, "New Relief for Pilots? It Depends", Wired, https://www.wired.com/2008/05/pilot-relief/, 2008, 2 pages.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/905,400 dated Jun. 9, 2021.
Corrected Notice of Allowability for U.S. Appl. No. 15/612,325 dated Mar. 17, 2021.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 17/088,272 dated May 25, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 2021.
International Search Report and Written Opinion from International Application No. PCT/US2021/027913 dated Jul. 12, 2021.
Issue Notification for U.S. Appl. No. 14/952,591 dated Jul. 28, 2021.
Issue Notification for U.S. Appl. No. 15/612,325 dated Mar. 24, 2021.
Issue Notification for U.S. Appl. No. 29/624,661 dated Aug. 4, 2021.
Non-Final Office Action for U.S. Appl. No. 16/905,400 dated Jul. 22, 2021.
Notice of Allowance for U.S. Appl. No. 14/952,591 dated Apr. 5, 2021.
Notice of Allowance for U.S. Appl. No. 14/952,591 dated Jul. 8, 2021.
Notice of Allowance for U.S. Appl. No. 17/088,272 dated Aug. 5, 2021.
Notice of Allowance for U.S. Appl. No. 29/624,661 dated Apr. 28, 2021.
Notice of Allowance for U.S. Appl. No. 29/694,002 dated Apr. 29, 2021.
Restriction Requirement for U.S. Appl. No. 16/478,180 dated May 25, 2021.
U.S. Appl. No. 17/330,657, filed May 26, 2021.
U.S. Appl. No. 17/378,015, filed Jul. 16, 2021.
U.S. Appl. No. 17/444,825, filed Aug. 10, 2021.
U.S. Appl. No. 62/938,447, filed Nov. 21, 2019.
U.S. Appl. No. 63/067,542, filed Aug. 19, 2020.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
Memorandum Order, Feb. 2021, 14 pgs.
Boehringer CareDry System—Second Generation for Non-Invasive Urinary Management for Females, Mar. 2021, 3 pgs.
Hollister, "Retracted Penis Pouch by Hollister", Vitality Medical.com, https://www.vitalitymedical.com/hollister-retracted-penis-pouch.html last accessed Jun. 24, 2020, 6 pages.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027917 dated Aug. 19, 2021.
International Search Report and Written Opinion from International Application No. PCT/US2021/035181 dated Sep. 16, 2021.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/904,868 dated Oct. 5, 2021.

(56) References Cited

OTHER PUBLICATIONS

Non-Final Office Action for U.S. Appl. No. 17/330,657 dated Aug. 11, 2021.
Notice of Allowance for U.S. Appl. No. 17/088,272 dated Nov. 24, 2021.
Notice of Allowance for U.S. Appl. No. 17/330,657 dated Nov. 26, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/612,325, filed Jun. 2, 2017.
U.S. Appl. No. 16/245,726, filed Jan. 11, 2019.
U.S. Appl. No. 17/446,256, filed Aug. 27, 2021.
U.S. Appl. No. 17/446,654, filed Sep. 1, 2021.
U.S. Appl. No. 17/447,123 filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,560, filed Nov. 4, 2021.
U.S. Appl. No. 17/461,036, filed Aug. 30, 2021.
U.S. Appl. No. 17/501,591, filed Oct. 14, 2021.
U.S. Appl. No. 17/595,747, filed Nov. 23, 2021.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/877,558, filed Jul. 23, 2019.
U.S. Appl. No. 63/047,374, filed Jul. 2, 2020.
U.S. Appl. No. 63/073,545, filed Sep. 2, 2020.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/247,491, filed Sep. 23, 2021.
Advisory Action for U.S. Appl. No. 16/905,400 dated Feb. 16, 2022.
Corrected Notice of Allowability for U.S. Appl. No. 17/330,657 dated Dec. 9, 2021.
Final Office Action for U.S. Appl. No. 16/904,868 dated Mar. 10, 2022.
Final Office Action for U.S. Appl. No. 16/905,400 dated Dec. 9, 2021.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2021/015024 dated May 18, 2021.
International Search Report and Written Opinion from International Application No. PCT/US2021/024162 dated Jul. 8, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048661 dated Feb. 14, 2022.
International Search Report and Written Opinion from International Application No. PCT/US2021/056566 dated Feb. 11, 2022.
Non-Final Office Action for U.S. Appl. No. 16/245,726 dated Jan. 21, 2022.
Non-Final Office Action for U.S. Appl. No. 16/449,039 dated Dec. 8, 2021.
Non-Final Office Action for U.S. Appl. No. 29/741,751 dated Jan. 18, 2022.
Notice of Allowance for U.S. Appl. No. 17/088,272 dated Mar. 4, 2022.
Notice of Allowance for U.S. Appl. No. 17/330,657 dated Mar. 16, 2022.
Restriction Requirement for U.S. Appl. No. 16/433,773 dated Dec. 7, 2021.
U.S. Appl. No. 15/384,196, filed Dec. 19, 2016.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 62/853,279, filed May 28, 2019.
U.S. Appl. No. 62/864,656, filed Jun. 21, 2019.
U.S. Appl. No. 62/883,172, filed Aug. 6, 2019.
U.S. Appl. No. 62/935,337, filed Nov. 14, 2019.
U.S. Appl. No. 63/030,685, filed May 27, 2020.
U.S. Appl. No. 63/073,553, filed Sep. 2, 2020.
U.S. Appl. No. 63/124,271, filed Dec. 11, 2020.
U.S. Appl. No. 63/133,892, filed Jan. 5, 2021.
U.S. Appl. No. 63/138,878, filed Jan. 19, 2021.
U.S. Appl. No. 63/146,946, filed Feb. 8, 2021.
U.S. Appl. No. 63/159,186, filed Mar. 10, 2021.
U.S. Appl. No. 63/193,891, filed May 27, 2021.
U.S. Appl. No. 63/208,262, filed Jun. 8, 2021.
U.S. Appl. No. 63/215,017, filed Jun. 25, 2021.
U.S. Appl. No. 63/228,244, filed Aug. 2, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml vol. Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.connivinyl-dust-cover-janonne-74181000, 2020, 2 pages.
Ali, "Sustainability Assessment: Seventh Generation Diapers versus gDiapers", The University of Vermont, Dec. 6, 2011, pp. 1-31.
Advisory Action for U.S. Appl. No. 16/904,868 dated Jun. 15, 2022.
Final Office Action for U.S. Appl. No. 16/452,145 dated Mar. 25, 2022.
Final Office Action for U.S. Appl. No. 16/452,258 dated Jun. 14, 2022.
Final Office Action for U.S. Appl. No. 16/478,180 dated Jun. 22, 2022.
International Search Report and Written Opinion from International Application No. PCT/US2020/057562 dated Jan. 27, 2021.
International Search Report and Written Opinion from International Application No. PCT/US2021/026607 dated Jul. 29, 2021.
International Search Report and Written Opinion from International Application No. PCT/US2021/048211 dated Dec. 22, 2021.
International Search Report and Written Opinion from International Application No. PCT/US2021/049404 dated Jan. 18, 2022.
International Search Report and Written Opinion from International Application No. PCT/US2021/051456 dated Jan. 19, 2022.
International Search Report and Written Opinion from International Application No. PCT/US2021/053593 dated Apr. 11, 2022.
International Search Report and Written Opinion from International Application No. PCT/US2021/055515 dated Jan. 28, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.

(56) References Cited

OTHER PUBLICATIONS

International Search Report and Written Opinion from International Application No. PCT/US2022/011281 dated Apr. 25, 2022.
International Search Report and Written Opinion from International Application No. PCT/US2022/011419 dated Jun. 7, 2022.
International Search Report and Written Opinion from International Application No. PCT/US2022/012794 dated May 3, 2022.
International Search Report and Written Opinion from International Application No. PCT/US2022/015471 dated May 16, 2022.
International Search Report and Written Opinion from International Application No. PCT/US2022/016942 dated Jun. 8, 2022.
International Search Report and Written Opinion from International Application No. PCT/US2022/018170 dated May 31, 2022.
International Search Report and Written Opinion from International Application No. PCT/US2022/019254 dated Jun. 7, 2022.
Issue Notification for U.S. Appl. No. 17/088,272 dated Jun. 15, 2022.
Issue Notification for U.S. Appl. No. 17/330,657 dated Jun. 22, 2022.
Non-Final Office Action for U.S. Appl. No. 16/369,676 dated Mar. 31, 2022.
Non-Final Office Action for U.S. Appl. No. 16/433,773 dated Apr. 21, 2022.
Non-Final Office Action for U.S. Appl. No. 16/905,400 dated Apr. 27, 2022.
Notice of Allowance for U.S. Appl. No. 29/741,751 dated Jun. 9, 2022.
U.S. Appl. No. 17/394,055, filed Aug. 4, 2021.
U.S. Appl. No. 17/412,864, filed Aug. 26, 2021.
U.S. Appl. No. 17/453,260, filed Nov. 2, 2021.
U.S. Appl. No. 17/494,578, filed Oct. 5, 2021.
U.S. Appl. No. 17/654,156, filed Mar. 9, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914 filed May 25, 222.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 62/923,279, filed Oct. 18, 2019.
U.S. Appl. No. 62/926,767, filed Oct. 28, 2019.
U.S. Appl. No. 62/967,977, filed Jan. 30, 2020.
U.S. Appl. No. 63/008,112, filed Apr. 10, 2020.
U.S. Appl. No. 63/033,310, filed Jun. 2, 2020.
U.S. Appl. No. 63/071,821, filed Aug. 28, 2020.
U.S. Appl. No. 63/088,539, filed Oct. 7, 2020.
U.S. Appl. No. 63/094,646, filed Oct. 21, 2020.
U.S. Application No. 63/109,084 filed Nov. 3, 2020.
U.S. Application No. 63/159,280 filed Mar. 10, 2021.
U.S. Application No. 63/191,558 filed May 21, 2021.
U.S. Application No. 63/192,289 filed May 24, 2021.
U.S. Application No. 63/230,897 filed Aug. 9, 2021.
U.S. Application No. 63/299,208 filed Jan. 13, 2022.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", Pnas, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Tsipenyuk, et al., "Use of biomimetic hexagonal surface texture in friction against lubricated skin", Journal of the Royal Society—Interface, 2014, pp. 1-6.
Advisory Action for U.S. Appl. No. 16/452,258 dated Oct. 26, 2022.
Advisory Action for U.S. Appl. No. 16/478,180 dated Sep. 21, 2022.
Final Office Action for U.S. Appl. No. 16/433,773 dated Oct. 25, 2022.
Final Office Action for U.S. Appl. No. 16/449,039 dated Aug. 1, 2022.
Final Office Action for U.S. Appl. No. 17/662,700 dated Sep. 30, 2022.
International Search Report and Written Opinion from International Application No. PCT/IB2021/057173 dated Nov. 5, 2021.
International Search Report and Written Opinion from International Application No. PCT/US2021/039866 dated Oct. 7, 2021.
International Search Report and Written Opinion from International Application No. PCT/US2022/011421 dated Jun. 13, 2022.
International Search Report and Written Opinion from International Application No. PCT/US2022/014285 dated Sep. 28, 2022.
International Search Report and Written Opinion from International Application No. PCT/US2022/015073 dated Sep. 8, 2022.
International Search Report and Written Opinion from International Application No. PCT/US2022/015492 dated Apr. 26, 2022.
International Search Report and Written Opinion from International Application No. PCT/US2022/015781 dated May 5, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
International Search Report and Written Opinion from International Application No. PCT/US2022/026667 dated Aug. 22, 2022.
Non-Final Office Action for U.S. Appl. No. 17/662,700 dated Jul. 22, 2022.
Notice of Allowance for U.S. Appl. No. 16/905,400 dated Aug. 17, 2022.
Notice of Allowance for U.S. Appl. No. 17/461,036 dated Oct. 6, 2022.
U.S. Appl. No. 14/433,773, filed Apr. 3, 2020.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 62/967,158, filed Jan. 26, 2020.
U.S. Appl. No. 62/991,754, filed Mar. 19, 2020.
U.S. Appl. No. 63/241,328, filed Sep. 7, 2021.

\* cited by examiner

300

302
Fluidically couple fluid discharge end of tube of a urine collecting apparatus to fluid receptacle

304
Fluidically couple a fluid discharge end of tube to a source of vacuum to assist in withdrawing urine via the tube from a reservoir of the urine collecting apparatus

306
Dispose urine collecting apparatus in operative relationship with urethral opening of the user, with head of user's penis disposed through opening into cavity at least partially defined by a membrane of the urine collecting apparatus

308
Allow urine discharged from the penis to be received into the cavity, through the membrane, through the support, and into the reservoir of urine collecting apparatus

310
Allow urine to be withdrawn from reservoir via tube, out of a fluid discharge end of the tube

312
Allow urine to be collected in fluid receptacle

314
Remove urine collecting apparatus from user's penis

316
Dispose a second urine collecting apparatus with head of user's penis disposed through opening into cavity

602 — Fluidically couple fluid discharge end of tube of a urine collecting apparatus to fluid receptacle

604 — Fluidically couple a fluid discharge end of tube to a source of vacuum to assist in withdrawing urine via the tube from a reservoir of the urine collecting apparatus

606 — Dispose urine collecting apparatus in operative relationship with urethral opening of the user, with head of user's penis disposed through opening into cavity collectively defined by a fluid permeable membrane and a casing of the urine collecting apparatus

608 — Allow urine discharged from the penis to be received into the cavity, through the membrane, through the support, and into the reservoir of urine collecting apparatus

610 — Allow urine to be withdrawn from reservoir via tube, out of a fluid discharge end of the tube

612 — Allow urine to be collected in fluid receptacle

614 — Remove urine collecting apparatus from user's penis

616 — Dispose a second urine collecting apparatus with head of user's penis disposed through opening into cavity

FIG. 8

APPARATUS AND METHODS FOR RECEIVING DISCHARGED URINE

CROSS-REFERENCE TO RELATED APPLICATIONS

This application is a continuation of and claims priority to and the benefit of U.S. patent application Ser. No. 15/612,325, filed Jun. 2, 2017, entitled "Apparatus and Methods for Receiving Discharged Urine, which application is a continuation-in-part of and claims priority to and the benefit of U.S. patent application Ser. No. 15/221,106, filed Jul. 27, 2016, entitled "Male Urine Collection Device Using Wicking Material," and also a continuation-in-part of and claims priority to and the benefit of U.S. patent application Ser. No. 15/238,427, filed Aug. 16, 2016, entitled "Using Wicking Material to Collect Urine From a Male for Transport," the disclosures of all of which are incorporated herein by reference in their entirety.

TECHNICAL FIELD

The present disclosure relates generally to systems, apparatus, and methods for collecting and transporting urine away from the body of a person or animal.

BACKGROUND

The embodiments described herein relate generally to collecting and transporting urine away from the body of a person or animal. In various circumstances, a person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, however, urinary catheters can be uncomfortable, painful, and can lead to complications, such as infections. Additionally, bed pans, which are receptacles used for the toileting of bedridden patients, such as those in a health care facility, are sometimes used. Bed pans, however, can be prone to discomfort, spills, and other hygiene issues.

Males who suffer the most severe consequences of urinary incontinence, such as discomfort, rashes, and sores are typically elderly and often bedbound. They also require continuous assistance to maintain hygiene. Characteristics often found in these patients: they typically lay on their back, the size of the penis often decreases with age, skin rolls containing fat tissue cause the penis to recede, often pointing upward while in a laying position, patients have difficulty reaching the penis and manipulating devices. A urine capture device should be designed with reference to these characteristics.

Available solutions are typically for use while standing up (such as cups and funnels), with a urine discharge port opposite to the distal end of the penis. Other designs such as condom-style catheters are difficult for patients to manipulate, too often they are dimensionally incompatible; and they do not stay on reliably.

Thus, there is a need for a device capable of collecting urine from a person or animal, particularly a male, comfortably and with minimal contamination of the user and/or the surrounding area.

SUMMARY

A system is disclosed that is suitable for collecting and transporting urine away from the body of a person or animal, particularly a male. The disclosed system includes an assembly that may include a fluid impermeable casing, a fluid permeable support, a fluid permeable membrane, and a tube. The fluid impermeable casing can define an opening, an interior region, and a fluid outlet. The fluid permeable support can define a reservoir. The support can be disposed within the interior region. The fluid permeable membrane can be disposed on the support and cover at least a portion of the support. The fluid permeable membrane can at least partially define a cavity. The tube can have a first end disposed in the elongated reservoir and can extend through the fluid outlet to a second, fluid discharge end. The apparatus is configured to be disposed with a user's penis disposed through the opening and with the urethral opening of the penis disposed within the cavity, to receive urine discharged from the urethral opening through the membrane, the support, and into the reservoir, and to have the received urine withdrawn from the reservoir via the tube and out of the fluid discharge end of the tube.

BRIEF DESCRIPTION OF THE DRAWINGS

FIG. 4 is a flowchart illustrating a method of using an assembly to collect urine from a user, according to an embodiment.

FIG. 8 is a flowchart illustrating a method of using an assembly to collect urine from a user, according to an embodiment.

DETAILED DESCRIPTION

Figure 1:
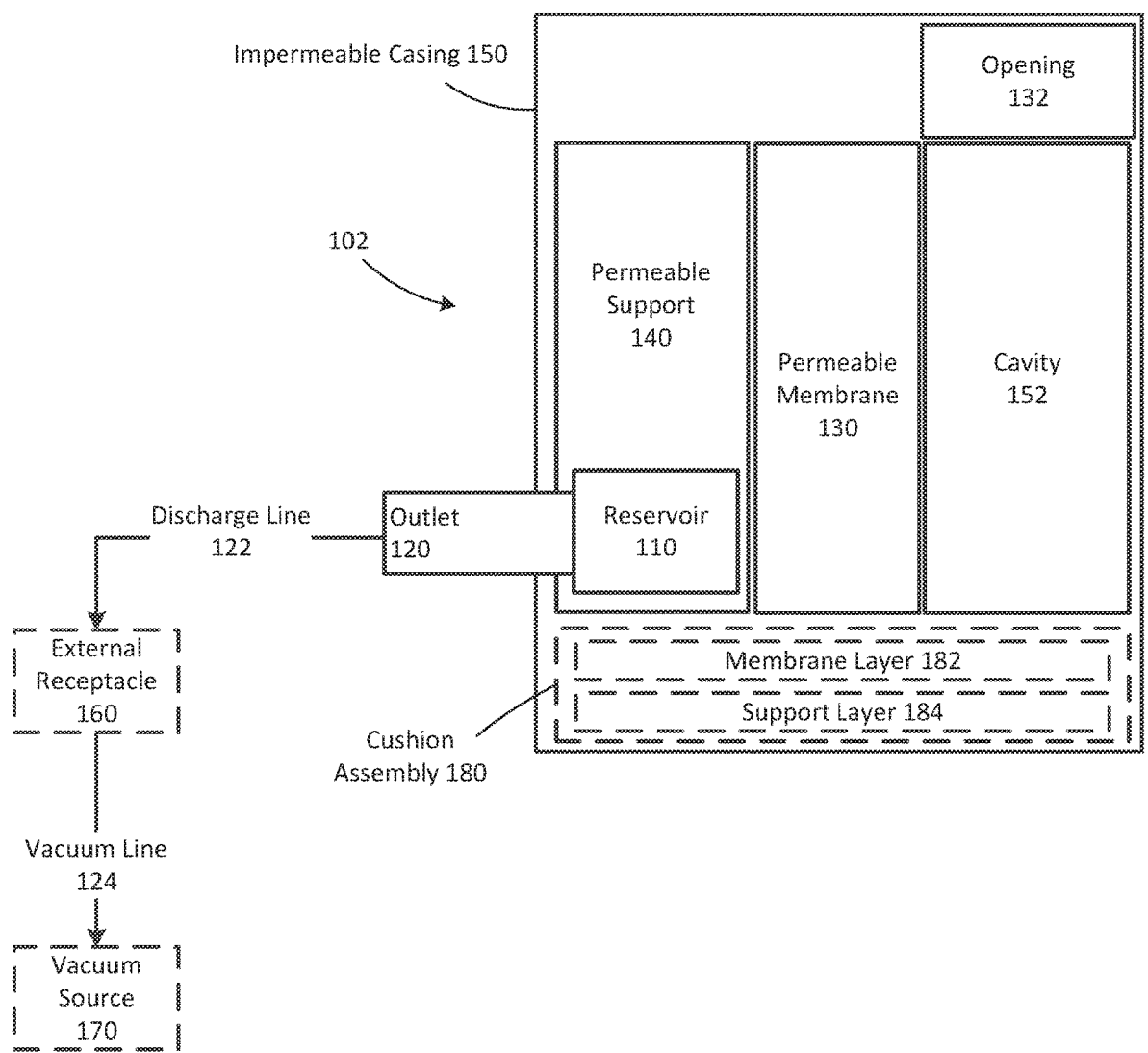
FIG. 1 is a schematic block diagram of a system, according to an embodiment.

A system is disclosed that is suitable for collecting and transporting urine away from the body of a person or animal, particularly a male. In some embodiments, the disclosed system includes an apparatus that may include a fluid impermeable casing, a fluid permeable support, a fluid permeable membrane, and a tube. The fluid impermeable casing can define an opening, an interior region, and a fluid outlet. The fluid permeable support can define a reservoir. The support can be disposed within the interior region. The fluid permeable membrane can be disposed on the support and cover at least a portion of the support. The fluid permeable membrane can at least partially define a cavity. The tube can have a first end disposed in the elongated reservoir and can extend through the fluid outlet to a second, fluid discharge end. The apparatus is configured to be disposed with a user's penis disposed through the opening and with the urethral opening of the penis disposed within the cavity, to receive urine discharged from the urethral opening through the membrane, the support, and into the reservoir, and to have the received urine withdrawn from the reservoir via the tube and out of the fluid discharge end of the tube.

In some embodiments, a method includes disposing in operative relationship with the urethral opening of a male user, a urine collecting apparatus. The method can include disposing in operative relationship with the urethral opening of a male user a urine collecting apparatus. The urine collecting apparatus can include a fluid impermeable casing, a fluid permeable support, a fluid permeable membrane, and a tube. The fluid impermeable casing can define an opening, an interior region, and a fluid outlet. The fluid permeable support can define a reservoir. The support can be disposed within the interior region. The fluid permeable membrane can be disposed on the support and can cover at least the portion of the support. The fluid permeable membrane can at least partially define a cavity. The tube can have a first end disposed in the elongated reservoir and extending through the fluid outlet to a second, fluid discharge end. The operative relationship can include the user's penis being disposed through the opening in the casing with the urethral opening of the penis disposed within the cavity. Urine discharged from the urethral opening can be allowed to be received through the membrane, the support, and into the reservoir. The received urine can be withdrawn from the reservoir via the tube and out of the fluid discharge end of the tube.

In some embodiments, an apparatus can include a fluid impermeable casing, a fluid permeable support, a fluid permeable membrane, and a tube. The fluid impermeable casing can define an opening, an interior region, and a fluid outlet. The fluid permeable support can be disposed within the interior region and have a first side facing the opening and a second side opposite the first side. The second side and the casing can collectively define a reservoir between the second side and the casing. The fluid permeable membrane can be disposed on the support between the opening and the first side of the support. The fluid permeable membrane and the casing can collectively define a cavity. The tube can have a first end disposed in the reservoir and can extend through the fluid outlet to a second, fluid discharge end. The apparatus can be configured to be disposed with a user's penis disposed through the opening with the urethral opening of the penis disposed within the cavity, to receive urine discharged from the urethral opening through the membrane, the support, and into the reservoir, and to have the received urine withdrawn from the reservoir via the tube and out of the fluid discharge end of the tube.

In some embodiments, a method can include disposing in operative relationship with the urethral opening of a male user a urine collecting apparatus. The urine collecting apparatus can include a fluid impermeable casing, a fluid permeable support, a fluid permeable membrane, and a tube. The fluid impermeable casing can define an opening, an interior region, and a fluid outlet. The fluid permeable support can be disposed within the interior region and have a first side facing the opening and a second side opposite the first side. The second side and the casing can collectively defining a reservoir between the second side and the casing. The fluid permeable membrane can be disposed on the support between the opening and the first side of the support. The fluid permeable membrane and the casing can collectively defining a cavity. The tube can have a first end disposed in the reservoir and can extend through the fluid outlet to a second, fluid discharge end. The operative relationship can include the user's penis being disposed through the opening in the casing with the urethral opening of the penis disposed within the cavity. Urine discharged from the urethral opening can be allowed to be received through the membrane, the support, and into the reservoir. The received urine can be allowed to be withdrawn from the reservoir via the tube and out of the fluid discharge end of the tube.

In some embodiments, a device can be used to so collect urine flowing from the penis of a person or an animal in such a manner that the urine can be readily transported from the device as the urine is being collected. The device can include a chamber assembly in which wicking material is disposed about porous material that is configured to form a chamber in which urine can be collected for transport. The chamber can have a port for receiving a tube so that urine collected within the chamber can be transported from the chamber by being drawn from the chamber when a partial vacuum is applied within the chamber via said received tube. The chamber assembly can be so dimensioned and configured that opposing portions of the assembly can be sufficiently adjacent as to define an opening through the which the head of a penis can be inserted. A layer of impermeable material can be so attached to the chamber assembly as to cover one side of the opening and thereby provide a receptacle for receiving the head of said inserted penis. Urine flowing from said penis can be drawn from the receptacle through the wicking material and the porous material into the chamber when said partial vacuum is applied within the chamber via said tube.

In some embodiments, a device can be used to so collect urine flowing from the penis of a person or an animal in such a manner that the urine can be transported from the device as the urine is being collected. The device can include a flexible layer of porous material, a flexible wicking material disposed on one side of the layer of porous material, and a flexible layer of impermeable material. The flexible layer of impermeable material can be secured to the periphery of the other side of the layer of porous material and so cover the other side of the layer of porous material as to define a chamber between the layer of porous material and the layer of impermeable material, within which chamber urine can be collected for transport. The chamber can have a port for receiving a tube so that urine collected within the chamber can be transported from the chamber by being drawn from the chamber when a partial vacuum is applied within the chamber via said received tube. The combination of the wicking material, the layer of porous material, and the layer of impermeable material can be so dimensioned and configured as to provide a receptacle for receiving the head of a penis. Urine flowing from said penis can be drawn from the receptacle through the wicking material and the porous material into the chamber when said partial vacuum is applied within the chamber via said received tube.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, nickel, iron, platinum, tin, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), and/or blends and copolymers thereof.

FIG. 1 is a schematic block diagram of a system 100. The system 100 includes an assembly 102. The assembly 102 includes a permeable membrane 130, a permeable support 140, and an impermeable casing 150 (also referred to herein as an "impermeable layer"). The permeable membrane 130 and the permeable support 140 can also be collectively referred to as a "chamber assembly." The permeable support 140 defines a reservoir 110 (also referred to herein as a "chamber"). The assembly 102 also includes an outlet 120 (also referred to herein as a "port") in fluidic communication with the reservoir 110. The permeable support 140 and the permeable membrane 130 can be arranged such that the permeable membrane 130 defines a cavity 152. The impermeable casing 150 defines an opening 132 such that the cavity 152 is accessible from the exterior of the assembly 100. The impermeable casing 150 can direct fluid toward the reservoir 110 and/or reduce and/or prevent fluid from exiting the assembly 102 except via the outlet 120. In some implementations, the assembly 102 can be arranged such that a fluid can flow through the opening 132, into the cavity 152, through the permeable membrane 130, through the permeable support 140, into the reservoir 110, and out of the outlet 120. In some implementations, the assembly 102 can be arranged such that a user's penis can be inserted through the opening 132 such that the user's urethral opening is disposed within the cavity 152 and a fluid can flow from the user's urethral opening, into the cavity 152, through the permeable membrane 130, through the permeable support 140, into the reservoir 110, and out of the outlet 120. In some implementations, the system 100 can include a discharge line 122 (also referred to herein as a "received tube"). The discharge line 122 can be fluidically coupled to an external receptacle 160. The external receptacle 160 can be in fluidic communication with a vacuum source 170 via a vacuum line 124. The discharge line 122 and the vacuum line 124 can both include flexible tubing, such as, for example, flexible plastic tubing.

More specifically, the impermeable casing 150 can define an interior region accessible via the opening 132. The permeable membrane 130 and the permeable support 140 (and thus, the reservoir 110) can be disposed within the interior region of the impermeable casing 150. The impermeable casing 150 can be any suitable shape. For example, in some implementations, the impermeable casing 150 can be bowl-shaped. In some implementations, the impermeable casing 150 can include a bottom surface and at least one sidewall. In some implementations, the at least one sidewall can define the opening 132 such that the opening 132 is opposite the bottom surface of the impermeable casing 150 and the interior region of the impermeable casing 150 is bounded (and collectively defined) by the bottom surface, the sidewall, and the opening 132. In some implementations, the impermeable casing 150 includes a top surface and the top surface defines the opening 132 opposite the bottom surface. In some implementations, the sidewall of the impermeable casing 150 is curved and continuous such that the impermeable casing 150 has a round (e.g., circular or ovalular) perimeter. In some implementations, the impermeable casing 150 can have any suitable shape and/or perimeter, such as the shape of an oblong, a square, or a triangle. In some implementations, the one or more sidewalls can be concave such that the one or more sidewalls can receive at least a portion of the permeable membrane 130 and the permeable support 140 as described in more detail below.

In some implementations, the impermeable casing 150 can be disposed around only a portion of the exterior sides of the permeable membrane 130 and/or the permeable support 140. In some implementations, the impermeable casing 150 can cover all of the exterior sides of the chamber assembly (i.e., the permeable membrane 130 and/or permeable support 140). In some implementations, the impermeable casing 150 can be disposed such that the impermeable casing 150 can wrap around the exterior surface of the permeable membrane 130 and/or the permeable support 140 and cover a portion of the interior side or sides of the chamber assembly (i.e., the permeable membrane 130 and/or the permeable support 140). In some implementations, the permeable membrane 130 and the permeable support 140 can be arranged to define a passageway with open ends (e.g., as a ring), and the impermeable casing 150 can be applied to one end and a side of the chamber assembly (i.e., the permeable membrane 130 and the permeable support 140) such that a cavity 152 is defined with the open end and the closed end. In some implementations, the chamber assembly can define the opening 132 rather than the impermeable casing 150. In some implementations, the portion of the impermeable casing 150 closing one end of the cavity 152 and partially defining the cavity 152 can have any suitable shape such that a portion or all of the head of a user's penis can be disposed within the cavity 152. For example, the portion of the impermeable casing 150 closing one end of the cavity 152 can be curved, convex, or flat.

In some implementations, the impermeable casing 150 can be attached to the chamber assembly (i.e., the permeable membrane 130 and the permeable support 140) via an adhesive. In some implementations, the impermeable casing 150 can be attached to the chamber assembly via any suitable retention mechanism, such as, for example, retainer clips or other fasteners. In some implementations, the impermeable casing 150 can be preshaped and the chamber assembly can be inserted into the impermeable casing 150 and retained in a particular shape by the impermeable casing 150. In some implementations, the impermeable casing 150 can be formed by, for example, elongate strips of adhesive tape such that the impermeable casing 150 can maintain the chamber assembly in the configuration defining the cavity 152.

The impermeable layer 150 can be impermeable to fluid, such as, for example, urine. In some implementations, the impermeable layer 150 can have a fluid transportation function and can assist in directing fluid towards the reservoir 110 and/or through the outlet 120 of the reservoir 110. In some implementations, the impermeable layer 150 can be formed as an integral, unitary structure. In other implementations, the impermeable layer 150 can be a multi-piece structure. The impermeable layer 150 can be a pre-molded (e.g., injection or blow molded) component. Alternatively, the impermeable layer 150 can be formed of a material, such as elongate strips of an adhesive tape, wrapped around at least a portion of the reservoir 110, a portion of the permeable support 140, and/or a portion of the permeable membrane 130. In some embodiments, the impermeable layer 150 can be formed of cardboard, pressed paper, and/or coated paper. In some embodiments, the impermeable layer 150 can be flexible.

The permeable membrane 130 can be formed of a material that has permeable properties with respect to liquids such as urine. The permeable properties can be wicking, capillary action, diffusion, or other similar properties or processes, and are referred to herein as "permeable" and/or "wicking." The permeable membrane 130 can have a high absorptive rate and a high permeation rate such that urine can be rapidly absorbed by the permeable membrane 130 and/or transported through the permeable membrane 130. In some implementations, the permeable membrane 130 can be flexible. In some implementations, the permeable membrane 130 can be a ribbed knit fabric. In some implementations, the permeable membrane 130 can be shaped as a tubular sleeve such that the permeable membrane 130 can be disposed around the permeable support 140. In some implementations, the permeable membrane 130 can include and/or have the moisture-wicking characteristic of gauze, felt, terrycloth, thick tissue paper, and/or a paper towel. In some implementations, the permeable membrane 130 can be soft and/or minimally abrasive such that the permeable membrane 130 does not irritate the skin of the user. The permeable membrane 130 can be configured to wick fluid away from the urethral opening and/or the skin of the user such that the dampness of the skin of the user is lessened and infections are prevented. Additionally, the wicking properties of the permeable membrane 130 can help prevent urine from leaking or flowing beyond the assembly (e.g., out of opening 132) onto, for example, a bed. In some implementations, the permeable membrane 130 can be formed of fine denier polyester fibers coated with a thermoplastic water-based binder system. The tensile strength can be, for example, about 45 lbs/inch$^2$ (measured using an Instron test method). The weight of a permeable membrane can be, for example, about 12 grams (measured using the Mettler Gram Scale). The thickness per ten permeable membranes can be, for example, about 2.5" (measured using the Gustin-Bacon/Measure-Matic).

The permeable support 140 can be positioned relative to the permeable membrane 130 such that the permeable support 140 maintains the permeable membrane 130 in a particular shape and allows for fluid, such as, for example, urine, to flow through the permeable membrane 130, through the permeable support 140, and into the reservoir 110. In some implementations, the permeable support 140 can be ring-shaped such that, when disposed within the impermeable casing 150, the cavity 152 is defined in the center of the ring-shaped permeable support 140. Said another way, an outer surface of the permeable support 140 on the inner portion of the "ring" can define the cavity 152. When the permeable membrane 130 is disposed on the permeable support 140, the permeable membrane 130 can define a portion of the boundaries of the cavity 152. When the permeable support 140 and the permeable membrane 130 are disposed within the impermeable casing 150, the cavity 152 can be aligned with the opening 132 of the impermeable casing 150. The reservoir 110 can be defined within or by the permeable support 140 such that the reservoir 110 is an elongated, ring-shaped reservoir.

In some implementations, the permeable support 140 can be shaped and/or formed as a complete or continuous ring or circle. In some implementations, the permeable support 140 can be shaped and/or formed as a partial circle and/or in a discontinuous C-shape with spaced ends. In some implementations, the permeable support 140 can be U-shaped. In some implementations, the chamber assembly can be dimensioned and configured such that opposing end portions of the chamber assembly are sufficiently adjacent or proximate as to define an opening through which the head of a penis can be inserted. In some implementations, the permeable support 140 can be formed of a bendable tube having two ends. The bendable tube can be arranged such that the two ends meet (e.g., forming a C-shape) and the permeable support 140 can be secured such that the permeable support 140 has a substantially circular shape. In some implementations, the outlet or port 120 can be positioned at the intersection of the two ends and in fluid communication with the elongated ring-shaped reservoir 110 defined by the permeable support 140. The discharge line 122 can be inserted through the outlet 120 (and thus through the impermeable casing 150 and the permeable support 140) and into fluid communication with the reservoir 110.

In some implementations, the permeable support 140 can be formed as an elongated tube such that the reservoir 110 extends through a portion or through the entire length of the elongated tube. The permeable support 140 can then be arranged and/or bent to form a ring such that the permeable support 140 defines the cavity 152 in the center of the ring. In some implementations, the inner diameter or other dimensions of the permeable support 140 can be sized such that the cavity 152 can receive a penis of a user such that a head of the penis can be partially or fully disposed within the cavity 152 when the penis is disposed within the opening 132 of the impermeable casing 150. Said another way, the shaft of the penis can be disposed within the opening 132 and the head of the penis can be fully disposed within the cavity 152, or the urethral opening of the head of the penis can be disposed within the cavity 152 and the head can be partially disposed within the cavity 152 and partially outside the cavity 152, with the opening 132 surrounding a portion of the head. In some implementations, the cavity 152 can be dimensioned to receive a head of a penis of a user such that urine can be received from the urethral opening of the penis within the cavity 152, by the permeable membrane 130, and/or by the permeable support 140 without urine splashing out of the opening 132.

In some implementations, the permeable support 140 can be configured to maintain the permeable membrane 130 against the skin of a penis of a user and/or near a urethral opening of a user. For example, the permeable support 140 can be shaped and sized such that the cavity 152 is slightly larger than a head or tip of a penis of a user. The permeable support 140 can include a portion having a curved or convex shape in contact with the permeable membrane 130 such that the permeable membrane 130 is also curved or convex. The permeable support 140 can support the permeable membrane 130 such that the permeable membrane 130 can rest against the skin of the head or tip of the penis with the urethral opening directed toward a bottom surface of the impermeable casing 150, and thus creating a comfortable and at least partially enclosed interface for engagement with the area of the body (e.g., the head and/or neck of a penis of a user) near the urethral opening.

In some implementations, the permeable support 140 can be made of a rigid plastic. In some implementations, the permeable support 140 can have any suitable shape and be formed of any suitable material. For example, the permeable support 140 can be flexible. Additionally, the permeable support 140 can be formed of aluminum, a composite of plastic and aluminum, some other metal and/or a composite of plastic and another metal. In some implementations, the permeable support 140 can be formed of a natural material, such as, for example, plant fibers (e.g., Greener Clean manufactured by 3M®). The natural material can include openings that allow fluid to flow through the natural material. In some embodiments, the permeable support 140 can be cylindrical and can define a lumen. In some embodiments, the permeable support 140 can be formed of perforated coated paper, such as tubular waxed paper.

The permeable support 140 can define one or more openings (e.g., an array of openings) to allow for fluid flow from the permeable membrane 130 to the reservoir 110. In some implementations, the permeable support 140 can be formed as a curved tube or a curved cylinder with one or more openings. In some implementations, the permeable support 140 can include membrane supports (e.g., struts) extending across an opening such that the opening is divided into an array of distinct slot-shaped openings. The membrane supports can be used to support the permeable membrane 130. For example, the membrane supports can maintain the shape of the permeable membrane 130 against the skin of a penis of a user and/or near a urethral opening of a user such that urine flowing from the urethral opening contacts and travels through the permeable membrane 130. In some implementations, the permeable support 140 can define several openings having a variety of shapes, such as a plurality of round openings. In some implementations, the permeable support 140 can be formed as a curved or ring-shaped cylinder of spun plastic (e.g., non-woven permeable nylon and polyester webbing) such that the permeable support 140 can have many openings. For example, a rectangular portion of spun plastic can be folded or rolled into a cylinder shape and then curved into a ring or U-shape for use in the assembly 102. In some implementations, the permeable support 140 can be formed of a porous material. For example, the permeable support 140 can be a porous glass ring-shaped tubular container defining frits. In other implementations, the permeable support 140 can define an opening in a sidewall of the permeable support 140 and the sidewall can be covered by a mesh screen defining many smaller openings. In some embodiments, the reservoir 110 can include any spaces and/or openings defined within the permeable support 140 (e.g., spaces within porous material or defined within spun plastic material).

The reservoir 110 can be any suitable shape and/or have any diameter (or other dimension) suitable for receiving and transporting urine during use of the system 100. In some implementations, the reservoir 110 can be sized such that the reservoir 110 is capable of collecting and temporarily holding a large or small amount of urine until the urine can be removed from the reservoir via the outlet 120. For example, the reservoir 110 can be sized such that the reservoir 110 is configured to hold a small amount of urine as may be released due to incontinence. In some implementations, the reservoir 110 can be sized such that the reservoir 110 is configured to hold a large amount of urine as may be released during voiding of a full bladder. In some implementations, the reservoir 110 can be sized such that the reservoir is configured to collect and hold a small or large amount of urine while the urine is simultaneously removed via, for example, gravity and/or a pump, such as the vacuum source 170. Said another way, the reservoir 110 can function as a sump and be sized such that the reservoir 110 can form a portion of a passageway for urine from the permeable membrane 130, through the permeable support 140, through the reservoir 110, and out of the outlet 120. In a condition where the flow rate of urine into the assembly 102 via the permeable membrane 130 is greater than the flow rate of urine through the discharge line 122, a temporary backup of urine may occur in the reservoir 110. Thus, the reservoir 110 can be sized to contain a volume of fluid that may temporarily accumulate due to the difference in flow rates into and out of the assembly 102. Although the outlet 120 is shown as extending from the side of the reservoir 110, in some implementations, the outlet 120 can extend from the bottom of the reservoir 110.

In some embodiments, the assembly 102 can optionally include a cushion assembly 180. The cushion assembly 180 can include a membrane layer 182 and a support layer 184 (also referred to herein as a "bed of porous material"). The membrane layer 182 can be formed of the same or a similar material as the permeable membrane 130 and can have the same or similar properties as the permeable membrane 130. For example, the membrane layer 182 can be configured to wick fluid (e.g., urine) away from a urethral opening of a user when a urethral opening of a user is position near or in contact with the membrane layer 182. The membrane layer 182 can also be permeable such that fluid (e.g., urine) can flow through the membrane layer 182 and to the permeable membrane 130 and/or the permeable support 140, into the reservoir 110, and through the outlet 120. The support layer 184 can be formed of the same or a similar material as the permeable support 140 and can have the same or similar properties as the permeable support 140. For example, the support layer 184 can be configured to maintain the membrane layer 182 near or in contact with the head of a user's penis when the head of the user's penis is disposed within the cavity 152 of the assembly 102. The support layer 184 can also be permeable such that fluid (e.g., urine) can flow through the membrane layer 182, through the support layer 184, and to the permeable membrane 130 and/or the permeable support 140, into the reservoir 110, and through the outlet 120. The cushion assembly 180 can be arranged within the impermeable casing 150 such that the cushion assembly 180 forms a boundary of the cavity 152 (e.g., the bottom of the cavity 152). The cushion assembly 180 can be positioned along a bottom surface of the impermeable casing 150 such that a user's penis can be placed in contact with the cushion assembly 180 and/or such that urine flowing from a user's urethral opening into the cavity 152 can flow into the cushion assembly 180 thereby reducing splashing. In some implementations, the cushion assembly 180 (and specifically the membrane layer 182) can be disposed within the impermeable casing 150 such that the cushion assembly 180 contacts the permeable membrane 130.

The external receptacle 160, via the discharge line 122, can collect fluid exiting the reservoir 110 through the outlet 120. The external receptacle 160 can be a sealed container. In some implementations, the external receptacle 160 can be disposable. In some implementations, the external receptacle 160 can be configured to be sterilized and reused.

In some implementations, gravity can cause fluid within the reservoir 110 to follow a flow path (i.e., the fluid flow path including the outlet 120 and the discharge line 122) from the reservoir 110 to the external receptacle 160. In some implementations, the vacuum source 170 can assist and/or provide the pressure differential needed to draw fluid voided from the urethral opening of a user into the permeable support 140, into the reservoir 110, and from the reservoir 110 into the external receptacle 160. The vacuum source 170 can be fluidically coupled to the external receptacle 160 via a vacuum line 124 such that gaseous fluid is drawn from the external receptacle 160 via the vacuum line 124. As a result of the decrease in pressure within the external receptacle 160 caused by the drawing of gaseous fluid out of the external receptacle 160, liquid and/or gaseous fluid can be drawn from the reservoir 110, through the outlet 120, through the discharge line 122, and into the external receptacle 160. In some implementations, the vacuum source 170 can apply sufficient suction to capture all or substantially all of the urine voided by a user in a variety of positions (e.g., when a male user is lying on his side or back).

The vacuum source 170 can have a sufficiently high vacuum strength and air volume transport rate such that rapid air and liquid aspiration is maintained over a portion of or the entire permeable membrane 130. In some implementations, the one or more openings of the permeable support 140 are distributed over an area that is slightly larger than the area of the permeable membrane 130 that is configured to be wetted by urine flow in operation. Thus, the partial vacuum created by the vacuum source 170 in combination with the one or more openings of the permeable support 140 and the permeable membrane 130 can draw the urine contacting the permeable membrane 130 into the assembly 102 and, specifically, into the reservoir 110. In some implementations, however, the one or more openings of the permeable support 140 should not be distributed over too large of an area of the permeable support 140 because the partial vacuum strength may be reduced, thereby reducing the urine collection rate and the efficiency of the system 100.

In some implementations, the vacuum source 170 can be a pump that is readily available, inexpensive, relatively quiet, and/or configured to run continuously. For example, the vacuum source 170 can be an aquarium aerator pump. The vacuum line 124 can be attached to the intake port of the aquarium aerator pump (rather than the exhaust port of the aerator) such that gaseous fluid is drawn into the aquarium aerator pump from the external receptacle 160 via the vacuum line 124. In some implementations, the necessary static vacuum of the system 100 is about 3-10 feet of water (10%-30% of one atmosphere; 80-250 mm Hg) with a free-flow rate of about 10-100 cubic centimeters per second. In some implementations, the necessary static vacuum of the system 100 is higher or lower depending on the size of the user and the expected rate of urine flow from the user and/or through the system 100. In some implementations, the discharge line 122 can be about 0.25" in diameter and the vacuum source 170 can be configured to cause about 500 cubic centimeters of urine to flow through the discharge line 122 to the external receptacle 160 over the duration of a typical urination event for a user, which may typically range from 10 to 20 seconds but may be shorter or longer, e.g., 5 to 90 seconds. In some implementations, the vacuum source 170 can include a wall-mounted vacuum system, such as is found in hospitals. In some implementations, a wall-mounted vacuum system can be configured to apply a vacuum of, for example, about 20 mm Hg to about 40 mm Hg. In some implementations, the vacuum source 170 can be powered by electrical AC or DC power. For example, in mobile applications when the user is away from an AC power source, such as when the user is using the system 100 during transportation via a wheel chair or motor vehicle, the vacuum source 170 can be powered by DC power.

In some implementations, urine collected by any of the systems and/or assemblies described herein can be sampled for analysis using urine strips. Urine test strips can be used to test a variety of health measures. Urine test strips can be configured to change color in response to being wetted with urine to indicate a particular measurement (i.e., the colors can correspond to known measurement scales). In some implementations, a urine test strip (not shown) can be inserted into the discharge line 122 such that urine flowing from the outlet 120 to the external receptacle 160 contacts the urine test strip. The discharge line 122 can be transparent such that data on the urine test strip can be read through a wall of the discharge line 122. In some implementations, the urine test strip can be disposed within the external receptacle 160 such that urine flowing into the external receptacle 160 contacts the urine test strip. The external receptacle 160 can be at least partially transparent such that the urine test strip can be read through a wall of the external receptacle 160.

In some implementations, a camera, such as a camera built into a portable communication device (e.g., a smartphone, an iPhone, or the like) can be used to read the data on the urine test strip. The camera can capture an image of the test strip and the image can be processed using, for example, a smartphone application. The data read from the urine test strip can be sent to a clinician for analysis and/or sent to a cloud-based address for physician access.

In some implementations, the system 100 can include a scale (not shown). For example, the scale can be disposed underneath the external receptacle 160 such that the scale is configured to measure the weight of fluid (e.g., urine) in the external receptacle 160. The data indicating the weight of the fluid that has been delivered to the external receptacle 160 via the discharge line 122 can be measured at different time intervals and processed to determine how much urine, for example, has been voided by a user of the system 100.

Although described as being intended for use by an adult male, in some implementations the system 100 can be used in adult, pediatric, male, female, and veterinary applications for animals of different species and sizes. In female applications, the assembly 102 can be placed between the legs or labia of the user and held snugly against the external urethra by the pressure of friction from the user's body, by the pressure of the legs or by such means as an undergarment, elastic strips, and/or adhesive tape. In male applications, the assembly 102 can be placed such that a penis of a user is disposed within the assembly 102 (e.g., within the cavity 152 formed within the assembly 102). A male user can use the assembly 102 in any suitable position, such as, for example, while lying on his back, lying on his side, sitting, or standing. In some implementations, the head of the penis of the male user can be placed in contact with the permeable membrane 130 and/or the membrane layer 182 during urination. In some implementations, the head of the penis of the male user can be disposed at least partially within the cavity 452, but not placed in contact with the permeable membrane 430 and/or the membrane layer 182 during urination.

Figure 2:
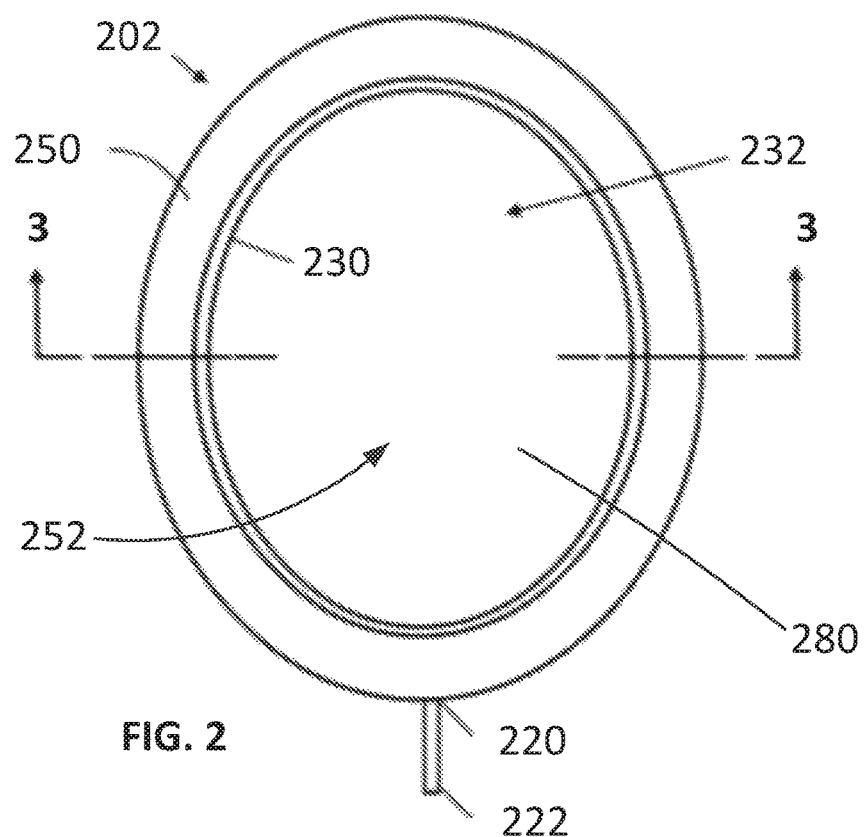
FIG. 2 is a top view of an assembly, according to an embodiment.
Figure 3:
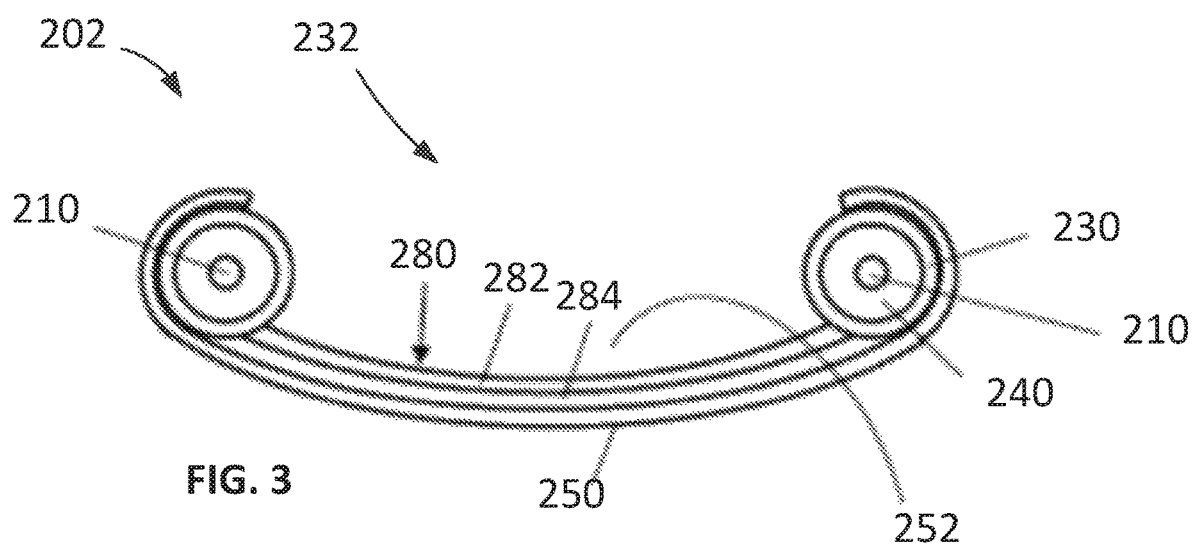
FIG. 3 is a cross-sectional view of the assembly of FIG. 2 taken along line 3-3 of FIG. 2.

FIG. 2 is a top view of an assembly 202. FIG. 3 is a cross-sectional view of the assembly 202 taken along line 3-3 in FIG. 2. The assembly 202 includes a permeable membrane 230, a permeable support 240, and a cushion assembly 280. The permeable membrane 230 and the permeable support 240 can also be collectively referred to as a "chamber assembly." The permeable membrane 230, the permeable support 240, and the cushion assembly 280 are disposed within an impermeable casing (also referred to herein as an "impermeable layer"). The permeable membrane 230, the permeable support 240, the cushion assembly 280, and the impermeable casing 250 can be the same or similar in structure and/or function to the permeable membrane 130, the permeable support 140, the cushion assembly 180, and the impermeable casing 150 described above with reference to the system 100. For example, the permeable support 240 defines a reservoir 210 (also referred to herein as a "channel"). The impermeable casing 250 defines an opening 232 (also referred to herein as a "port"). The assembly 202 also includes an outlet 220 in fluidic communication with the reservoir 210.

The permeable support 240 and the permeable membrane 230 can be arranged such that the permeable support 240 and/or the permeable membrane 230 collectively define a cavity 252 within the permeable membrane 230. The impermeable casing 250 can direct fluid toward the reservoir 210 and/or reduce and/or prevent fluid from exiting the assembly 202 except via the outlet 220. In some implementations, the assembly 202 can be arranged such that a fluid can flow through the opening 232, into the cavity 252, through the permeable membrane 230, through the permeable support 240, into the reservoir 210, and out of the outlet 220. In some implementations, the assembly 202 can be arranged such that a user's penis can be inserted through the opening 232 such that the user's urethral opening is disposed within the cavity 252 and a fluid can flow from the user's urethral opening, into the cavity 252, through the permeable membrane 230, through the permeable support 240, into the reservoir 210, and out of the outlet 220. A discharge line 222 (e.g., a tube) (also referred to herein as a "received tube") can extend through the outlet 220. A first end (not shown) of the discharge line 222 can be positioned within the reservoir 210, and the discharge line 222 can extend through the permeable support 240, the permeable membrane 230, and the impermeable casing 250 such that fluid in the reservoir 210 can be transported away from the assembly 202 via the discharge line 222. A second end of the discharge line 222 can be fluidically coupled to an external receptacle (e.g., external receptacle 160). The external receptacle can be in fluidic communication with a vacuum source (e.g., vacuum source 170) via a vacuum line (e.g., vacuum line 124). The discharge line 222 and the vacuum line can both include flexible tubing, such as, for example, flexible plastic tubing.

More specifically, the impermeable casing 250 can define an interior region accessible via the opening 232. The permeable membrane 230 and the permeable support 240 (and thus, the reservoir 210) can be disposed within the interior region of the impermeable casing 250. The impermeable casing 250 can be any suitable shape. For example, in some implementations, the impermeable casing 250 can be bowl-shaped. As shown in FIG. 3, the impermeable casing 250 can include a bottom surface and a sidewall. The sidewall can define the opening 232 such that the opening 232 is opposite the bottom surface of the impermeable casing 250 and the interior region of the impermeable casing 250 is bounded (and collectively defined) by the bottom surface, the sidewall, and the opening 232. The sidewall of the impermeable casing 250 can be curved and continuous such that the impermeable casing 250 has a round (e.g., circular or ovalular) perimeter. The sidewall can be concave such that the one or more sidewalls can receive at least a portion of the permeable membrane 230 and the permeable support 240 as shown in FIG. 3.

The impermeable layer 250 can be impermeable to fluid, such as, for example, urine. In some implementations, the impermeable layer 250 can have a fluid transportation function and can assist in directing fluid towards the reservoir 210 and/or through the outlet 220 of the reservoir 210. In some implementations, the impermeable layer 250 can be formed as an integral, unitary structure. In other implementations, the impermeable layer 250 can be a multi-piece structure. The impermeable layer 250 can be a pre-molded (e.g., injection or blow molded) component. Alternatively, the impermeable layer 250 can be formed of a material, such as elongate strips of an adhesive tape, wrapped around at least a portion of the reservoir 210, a portion of the permeable support 240, and/or a portion of the permeable membrane 230. In some embodiments, the impermeable layer 250 can be formed of cardboard, pressed paper, and/or coated paper. In some embodiments, the impermeable layer 250 can be flexible.

The permeable membrane 230 can be formed of a material that has permeable properties with respect to liquids such as urine. The permeable properties can be wicking, capillary action, diffusion, or other similar properties or processes, and are referred to herein as "permeable" and/or "wicking." The permeable membrane 230 can have a high absorptive rate and a high permeation rate such that urine can be rapidly absorbed by the permeable membrane 230 and/or transported through the permeable membrane 230. In some implementations, the permeable membrane 230 can be flexible. In some implementations, the permeable membrane 230 can be a ribbed knit fabric. In some implementations, the permeable membrane 230 can be shaped as a tubular sleeve such that the permeable membrane 230 can be disposed around the permeable support 240. In some implementations, the permeable membrane 230 can include and/or have the moisture-wicking characteristic of gauze, felt, terrycloth, thick tissue paper, and/or a paper towel. In some implementations, the permeable membrane 230 can be soft and/or minimally abrasive such that the permeable membrane 230 does not irritate the skin of the user. The permeable membrane 230 can be configured to wick fluid away from the urethral opening and/or the skin of the user such that the dampness of the skin of the user is lessened and infections are prevented. Additionally, the wicking properties of the permeable membrane 230 can help prevent urine from leaking or flowing beyond the assembly (e.g., out of opening 232) onto, for example, a bed. In some implementations, the permeable membrane 230 can be formed of fine denier polyester fibers coated with a thermoplastic water-based binder system. The tensile strength can be, for example, about 45 lbs/inch$^2$ (measured using an Instron test method). The weight of a permeable membrane can be, for example, about 12 grams (measured using the Mettler Gram Scale). The thickness per ten permeable membranes can be, for example, about 2.5" (measured using the Gustin-Bacon/Measure-Matic).

The permeable support 240 can be positioned relative to the permeable membrane 230 such that the permeable support 240 maintains the permeable membrane 230 in a particular shape and allows for fluid, such as, for example, urine, to flow through the permeable membrane 230, through the permeable support 240, and into the reservoir 210. As shown in FIG. 2, the permeable support 240 can be ring-shaped such that, when the permeable membrane 230 is disposed on the permeable support 240 and the permeable support 240 is disposed within the impermeable casing 250, the cavity 252 is defined in the center of the ring-shaped permeable support 240 and permeable membrane 230. Said another way, an outer surface of the permeable membrane 230 on the inner portion of the "ring" can define the cavity 252. As shown in FIGS. 2 and 3, the cavity 252 can be aligned with the opening 232 of the impermeable casing 250. The reservoir 210 can be defined within the permeable support 240 such that the reservoir 210 is an elongated, ring-shaped reservoir.

In some implementations, the permeable support 240 can be shaped and/or formed as a complete or continuous ring or circle. In some implementations, the permeable support 240 can be shaped and/or formed as a partial circle. In some implementations, the chamber assembly can be dimensioned and configured such that opposing end portions of the chamber assembly are sufficiently adjacent or proximate as to define an opening through which the head of a penis can be inserted. In some implementations, the permeable support 240 can be formed of a bendable tube having two ends. The bendable tube can be arranged such that the two ends meet (e.g., forming a C-shape) and the permeable support 240 can be secured such that the permeable support 240 has a substantially circular shape. In some implementations, the outlet or port 220 can be positioned at the intersection of the two ends and in fluid communication with the elongated ring-shaped reservoir 210 defined by the permeable support 240. The discharge line 222 can be inserted through the outlet 220 (and thus through the impermeable casing 250 and the permeable support 240) and into fluid communication with the reservoir 210.

In some implementations, the permeable support 240 can be formed as an elongated tube such that the reservoir 210 extends through a portion or through the entire length of the elongated tube. The permeable support 240 can then be arranged and/or bent to form a ring such that the permeable support 240 defines the cavity 252 in the center of the ring. In some implementations, the inner diameter or other dimensions of the permeable support 240 can be sized such that the cavity 252 can receive a penis of a user such that a head of the penis can be partially or fully disposed within the cavity when the penis is disposed within the opening 232 of the impermeable casing 250. Said another way, the shaft of the penis can be disposed within the opening 232 and the head of the penis can be fully disposed within the cavity 252, or the urethral opening of the head of the penis can be disposed within the cavity 252 and the head can be partially disposed within the cavity 252 and partially outside the cavity 252, with the opening 232 surrounding a portion of the head. In some implementations, the cavity 252 can be dimensioned to receive a head of a penis of a user such that urine can be received from the urethral opening of the penis within the cavity 252, by the permeable membrane 230, and/or by the permeable support 240 without urine splashing out of the opening 232.

In some implementations, the permeable support 240 can be configured to maintain the permeable membrane 230 against the skin of a penis of a user and/or near a urethral opening of a user. For example, the permeable support 240 can be shaped and sized such that the cavity 252 is slightly larger than a head or tip of a penis of a user. The permeable support 240 can include a portion having a curved or convex shape in contact with the permeable membrane 230 such that the permeable membrane 230 is also curved or convex. The permeable support 240 can support the permeable membrane 230 such that the permeable membrane 230 can rest against the skin of the head or tip of the penis with the urethral opening directed toward a bottom surface of the impermeable casing 250, and thus creating a comfortable and at least partially enclosed interface for engagement with the area of the body (e.g., the head and/or neck of a penis of a user) near the urethral opening.

In some implementations, the permeable support 240 can be made of a rigid plastic. In some implementations, the permeable support 240 can have any suitable shape and be formed of any suitable material. For example, the permeable support 240 can be flexible. Additionally, the permeable support 240 can be formed of aluminum, a composite of plastic and aluminum, some other metal and/or a composite of plastic and another metal. In some implementations, the permeable support 240 can be formed of a natural material, such as, for example, plant fibers (e.g., Greener Clean manufactured by 3M®). The natural material can include openings that allow fluid to flow through the natural material. In some embodiments, the permeable support 240 can be cylindrical and can define a lumen. In some embodiments, the permeable support 240 can be formed of perforated coated paper, such as tubular waxed paper.

The permeable support 240 can define one or more openings (e.g., an array of openings) to allow for fluid flow from the permeable membrane 230 to the reservoir 210. In some implementations, the permeable support 240 can be formed as a curved tube or a curved cylinder with one or more openings. In some implementations, the permeable support 240 can include membrane supports (e.g., struts) extending across an opening such that the opening is divided into an array of distinct slot-shaped openings. The membrane supports can be used to support the permeable membrane 230. For example, the membrane supports can maintain the shape of the permeable membrane 230 against the skin of a penis of a user and/or near a urethral opening of a user such that urine flowing from the urethral opening contacts and travels through the permeable membrane 230. In some implementations, the permeable support 240 can define several openings having a variety of shapes, such as a plurality of round openings. In some implementations, the permeable support 240 can be formed as a curved or ring-shaped cylinder of spun plastic (e.g., non-woven permeable nylon and polyester webbing) such that the permeable support 240 can have many openings. For example, a rectangular portion of spun plastic can be folded or rolled into a cylinder shape and then curved into a ring for use in the assembly 202. In some implementations, the permeable support 240 can be formed of a porous material. For example, the permeable support 240 can be a porous glass ring-shaped tubular container defining frits. In other implementations, the permeable support 240 can define an opening in a sidewall of the permeable support 240 and the sidewall can be covered by a mesh screen defining many smaller openings. In some embodiments, the reservoir 210 can include any spaces and/or openings defined within the permeable support 240 (e.g., spaces within porous material or defined within spun plastic material).

The reservoir 210 can be any suitable shape and/or have any diameter (or other dimension) suitable for receiving and transporting urine during use of a system including the assembly 202. In some implementations, the reservoir 210 can be sized such that the reservoir 210 is capable of collecting and temporarily holding a large or small amount of urine until the urine can be removed from the reservoir via the outlet 220. For example, the reservoir 210 can be sized such that the reservoir 210 is configured to hold a small amount of urine as may be released due to incontinence. In some implementations, the reservoir 210 can be sized such that the reservoir 210 is configured to hold a large amount of urine as may be released during voiding of a full bladder. In some implementations, the reservoir 210 can be sized such that the reservoir is configured to collect and hold a small or large amount of urine while the urine is simultaneously removed via, for example, gravity and/or a pump, such as the vacuum source 270. Said another way, the reservoir 210 can function as a sump and be sized such that the reservoir 210 can form a portion of a passageway for urine from the permeable membrane 230, through the permeable support 240, through the reservoir 210, and out of the outlet 220. In a condition where the flow rate of urine into the assembly 202 via the permeable membrane 230 is greater than the flow rate of urine through the discharge line 222, a temporary backup of urine may occur in the reservoir 210. Thus, the reservoir 210 can be sized to contain a volume of fluid that may temporarily accumulate due to the difference in flow rates into and out of the assembly 202.

Although the outlet 220 is shown as extending from the side of the reservoir 210, in some implementations, the outlet 220 can extend from the bottom of the reservoir 210.

The cushion assembly 280 can include a membrane layer 282 and a support layer 284 (also referred to herein as a "bed of porous material"). The membrane layer 282 can be formed of the same or a similar material as the permeable membrane 230 and can have the same or similar properties as the permeable membrane 230. For example, the membrane layer 282 can be configured to wick fluid (e.g., urine) away from a urethral opening of a user when a urethral opening of a user is position near or in contact with the membrane layer 282. The membrane layer 282 can also be permeable such that fluid (e.g., urine) can flow through the membrane layer 282 and to the permeable membrane 230 and/or the permeable support 240, into the reservoir 210, and through the outlet 220. The support layer 284 can be formed of the same or a similar material as the permeable support 240 and can have the same or similar properties as the permeable support 240. For example, the support layer 284 can be configured to maintain the membrane layer 282 near or in contact with the head of a user's penis when the head of the user's penis is disposed within the cavity 252 of the assembly 202. The support layer 284 can also be permeable such that fluid (e.g., urine) can flow through the membrane layer 282, through the support layer 284, and to the permeable membrane 230 and/or the permeable support 240, into the reservoir 210, and through the outlet 220. The cushion assembly 280 can be arranged within the impermeable casing 250 such that the cushion assembly 280 forms a boundary of the cavity 252 (e.g., the bottom of the cavity 252). The cushion assembly 280 can be positioned along a bottom surface of the impermeable casing 250 such that a user's penis can be placed in contact with the cushion assembly 280 and/or such that urine flowing from a user's urethral opening into the cavity 252 can flow into the cushion assembly 280 thereby reducing splashing. In some implementations, the cushion assembly 280 (and specifically the membrane layer 282) can be disposed within the impermeable casing 250 such that the cushion assembly 280 contacts the permeable membrane 230.

FIG. 4 is a flowchart illustrating a method of using an assembly to collect urine from a user, according to an embodiment. The method 300 optionally includes, at 302, fluidically coupling a discharge end of a tube of a urine collecting apparatus to a fluid receptacle. The method 300 optionally further includes, at 304, fluidically coupling the discharge end of the tube of the urine collecting apparatus to a source of vacuum.

The method 300 further includes, at 306, disposing the urine collecting apparatus in operative relationship with the urethral opening of the user, with a head of a penis of a male user (e.g. human or animal) disposed through an opening and into a cavity at least partially defined by a membrane of the urine collecting apparatus. The urine collecting apparatus can be the same or similar in structure and/or function to any of the urine collecting apparatus described herein, such as, for example, the assembly 102 in FIG. 1 and/or the assembly 202 in FIG. 2. For example, the urine collecting apparatus can include a fluid impermeable casing, a fluid permeable support, a fluid permeable membrane, and a tube. The fluid impermeable casing can define an opening, an interior region, and a fluid outlet. The fluid permeable support can define a reservoir. The fluid permeable support can also be disposed within the interior region of the fluid impermeable casing. The fluid permeable membrane can be disposed on the support and cover at least a portion of the support. The fluid permeable membrane can at least partially define a cavity aligned with the opening defined in the fluid impermeable casing. The tube can have a first end disposed in the elongated reservoir and extend through the fluid outlet to a second, fluid discharge end. The assembly can be arranged such that a fluid can flow into the cavity from the urethral opening of the user's penis, flow through the fluid permeable membrane and the fluid permeable support, collect in the reservoir, and flow out of the outlet.

The method 300 also includes, at 308, allowing urine discharged from the penis to be received into the cavity, through the membrane, through the support, and into the reservoir.

The method 300 also includes, at 310, allowing the received urine to be withdrawn from the reservoir via the tube and out of the fluid discharge end of the tube.

The method 300 optionally includes, at 312, allowing the withdrawn urine to be collected in the fluid receptacle.

The method 300 optionally includes, at 314, removing the urine collecting apparatus from the penis of the user. Thus, the urine collecting apparatus can capture and transport urine from a user without having to attach a catheter to the urethral opening of the user's penis. In some implementations, the urine can flow against gravity during collection.

Finally, the method 300 optionally includes, at 316, disposing a second urine collecting apparatus in operative relationship with the urethral opening of the user, with the head of the penis of the user disposed through the opening and into the cavity of the urine collecting apparatus.

Figure 5:
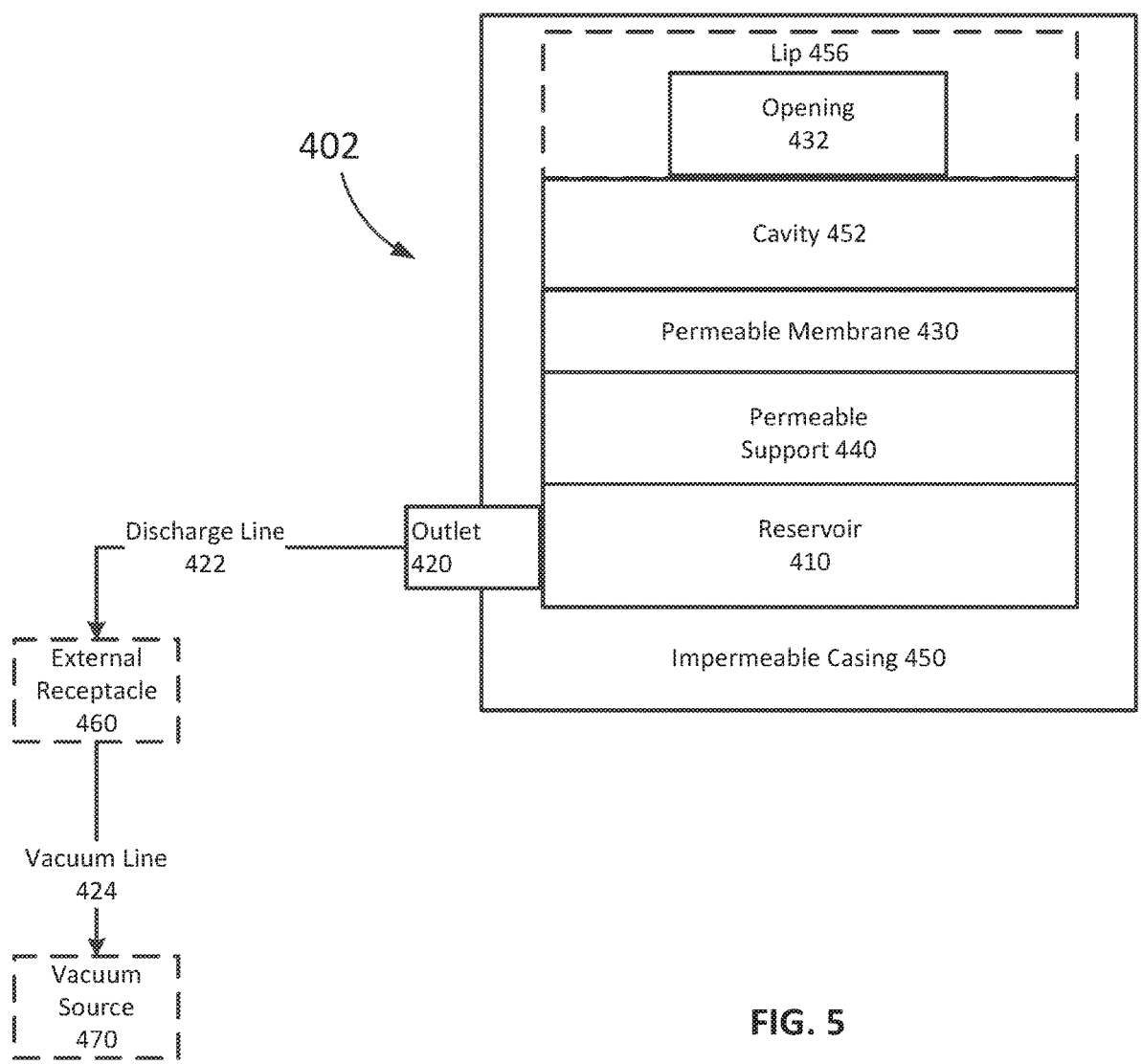
FIG. 5 is a schematic block diagram of a system, according to an embodiment.

FIG. 5 is a schematic block diagram of a system 400. The system 400 includes an assembly 402. The assembly 402 includes a permeable membrane 430, a permeable support 440, and an impermeable casing 450 (also referred to herein as an "impermeable layer"). The permeable support 440 and the impermeable casing 450 collectively define a reservoir 410 (also referred to herein as a "chamber"). The assembly 402 also includes an outlet 420 (also referred to herein as a "port") in fluidic communication with the reservoir 410. The permeable support 440 and the permeable membrane 430 can be arranged such that the permeable membrane 430 defines a cavity 452 within the impermeable casing 450. The impermeable casing 450 defines an opening 432 such that the cavity 452 is accessible from an exterior of the assembly 402. The impermeable casing 450 can direct fluid toward the reservoir 410 and/or reduce and/or prevent fluid from exiting the assembly 402 except via the outlet 420. In some implementations, the assembly 402 can be arranged such that a fluid can flow through the opening 432, into the cavity 452, through the permeable membrane 430, through the permeable support 440, into the reservoir 410, and out of the outlet 420. In some implementations, the assembly 402 can be arranged such that a user's penis can be inserted through the opening 432 such that the user's urethral opening is disposed within the cavity 452 and a fluid can flow from the user's urethral opening, into the cavity 452, through the permeable membrane 430, through the permeable support 440, into the reservoir 410, and out of the outlet 420. In some implementations, the system 400 can include a discharge line 422 (also referred to herein as a "received tube"). The discharge line 422 can be fluidically coupled to an external receptacle 460. The external receptacle 460 can be in fluidic communication with a vacuum source 470 via a vacuum line 424. The discharge line 422 and the vacuum line 424 can both include flexible tubing, such as, for example, flexible plastic tubing.

More specifically, the impermeable casing 450 can define an interior region accessible via the opening 432. The permeable membrane 430 and the permeable support 440 can be disposed within the interior region of the impermeable casing 450. The impermeable casing 450 can be any suitable shape. For example, in some implementations, the impermeable casing 450 can be bowl-shaped. In some implementations, the impermeable casing 450 can include a bottom surface and at least one sidewall. In some implementations, the opening 432 can be opposite a bottom surface of the impermeable casing 450. In some implementations, the opening 432 can be any suitable shape and/or size. In some implementations, the impermeable casing 450 can optionally include a lip 456 such that the opening 432 is bounded and defined at least partially by the lip 456. The lip 456 can partially or completely surround the opening 432. In some implementations, the lip 456 can be shaped and sized such that the lip 456 can reduce the potential of urine flowing out of the opening 432 and/or such that the risk of splashing of urine through the opening 432 is reduced.

In some implementations, the opening 432 has a width and/or length similar in size to the diameter of a user's penis. In some implementations, the opening 432 is larger in width and/or length than the diameter than a user's penis. In some implementations, the opening 432 can be, for example, circular or ovalular. In some implementations, the opening 432 can have any suitable shape. Similarly, the impermeable casing 450 can have any suitable shape and/or perimeter shape, such as the shape of, for example, an oblong, square, triangle, circle, oval, or an irregular shape. For example, the opening 432 (and the impermeable casing 450) can have a rounded or semi-circular first portion and a second portion that tapers from a first side adjacent to the first portion having a first width to a second width smaller than the first width. In some implementations, the shape of the opening 432 can be the same or similar as the perimeter shape of the top of the impermeable casing 450.

In some implementations, the permeable support 440 can have a bottom side with a periphery. The periphery can be secured to the impermeable casing 450. In some implementations, the periphery can be secured (e.g., via adhesive) to a portion of the impermeable casing 450 adjacent a top edge of the impermeable casing. In some implementations, the impermeable casing 450 can extend upward beyond the location to which the periphery of the permeable support 540 is attached. In some implementations, the impermeable casing 450 can be attached to the permeable support 440 via any suitable retention mechanism, such as, for example, retainer clips or other fasteners. In some implementations, the permeable support 440 and the permeable membrane 430 can be placed within the impermeable casing without additional coupling mechanisms.

The impermeable layer 450 can be impermeable to fluid, such as, for example, urine. In some implementations, the impermeable layer 450 can have a fluid transportation function and can assist in directing fluid towards the reservoir 410 and/or through the outlet 420 of the reservoir 410. In some implementations, the impermeable layer 450 can be formed as an integral, unitary structure. In other implementations, the impermeable layer 450 can be a multi-piece structure. The impermeable layer 450 can be a pre-molded (e.g., injection or blow molded) component. Alternatively, the impermeable layer 450 can be formed of a material, such as elongate strips of an adhesive tape, wrapped around at least a portion of the reservoir 410, a portion of the permeable support 440, and/or a portion of the permeable membrane 430. In some embodiments, the impermeable layer 450 can be formed of cardboard, pressed paper, and/or coated paper. In some embodiments, the impermeable layer 450 can be flexible.

The permeable membrane 430 can be formed of a material that has permeable properties with respect to liquids such as urine. The permeable properties can be wicking, capillary action, diffusion, or other similar properties or processes, and are referred to herein as "permeable" and/or "wicking." The permeable membrane 430 can have a high absorptive rate and a high permeation rate such that urine can be rapidly absorbed by the permeable membrane 430 and/or transported through the permeable membrane 430. In some implementations, the permeable membrane 430 can be flexible. In some implementations, the permeable membrane 430 can be a ribbed knit fabric. In some implementations, the permeable membrane 430 can include and/or have the moisture-wicking characteristic of gauze, felt, terrycloth, thick tissue paper, and/or a paper towel. In some implementations, the permeable membrane 430 can be soft and/or minimally abrasive such that the permeable membrane 430 does not irritate the skin of the user. The permeable membrane 430 can be configured to wick fluid away from the urethral opening and/or the skin of the user such that the dampness of the skin of the user is lessened and infections are prevented. Additionally, the wicking properties of the permeable membrane 430 can help prevent urine from leaking or flowing beyond the assembly (e.g., out of opening 432) onto, for example, a bed. In some implementations, the permeable membrane 430 can be formed of fine denier polyester fibers coated with a thermoplastic water-based binder system. The tensile strength can be, for example, about 45 lbs/inch$^2$ (measured using an Instron test method). The weight of a permeable membrane can be, for example, about 12 grams (measured using the Mettler Gram Scale). The thickness per ten permeable membranes can be, for example, about 2.5" (measured using the Gustin-Bacon/Measure-Matic).

The permeable support 440 can be positioned relative to the permeable membrane 430 such that the permeable support 440 maintains the permeable membrane 430 in a particular shape and allows for fluid, such as, for example, urine, to flow through the permeable membrane 430, through the permeable support 440, and into the reservoir 410. In some implementations, the permeable membrane 430 can be disposed on a first, upper side of the permeable support 440, and the second, bottom side of the permeable support 440 can define a boundary of the reservoir 410. In some implementations, the permeable support 440 can have a concave shape such that, when disposed within the impermeable casing 450, the cavity 452 has a concave bottom. When the permeable membrane 430 is disposed on the permeable support 440, the permeable membrane 430 can define a portion of the bottom and/or side boundaries of the cavity 452. When the permeable support 440 and the permeable membrane 430 are disposed within the impermeable casing 450, the cavity 452 can be aligned with the opening 432 of the impermeable casing 450. The reservoir 410 can be defined by the permeable support 440 and the impermeable casing 450 such that the reservoir 410 is concave and has any suitable shape and/or dimensions.

In some implementations, the permeable support 440 and/or the permeable membrane 430 can be any suitable shape and/or size. In some implementations, the permeable support 440 and the permeable membrane 430 can have the same or similar shape and dimensions. In some implementations, the permeable support 440 and/or the permeable membrane 430 can be shaped such that the outer perimeter of the permeable support 440 and/or the permeable membrane 430 can be the same or similar to the outer perimeter of the top of the impermeable casing 450 and/or the opening 432. In some implementations, the dimensions of the permeable support 440 and/or the permeable membrane 430 can be sized such that the cavity 452 can receive a penis of a user such that a head of the penis can be partially or fully disposed within the cavity 452 (i.e., the shaft of the penis can be disposed within the opening 432 and the head of the penis can be fully disposed within the cavity 452, or the urethral opening of the head of the penis can be disposed within the cavity 452 and the head can be partially disposed within the cavity 452 and partially outside the cavity 452, with the opening 432 surrounding a portion of the head). In some implementations, the cavity 452 can be dimensioned to receive a head of a penis of a user such that urine can be received from the urethral opening of the penis within the cavity 452, by the permeable membrane 430, and/or by the permeable support 440 without urine splashing out of the opening 432.

In some implementations, the permeable support 440 can be configured to maintain the permeable membrane 430 against the skin of a penis of a user and/or near a urethral opening of a user. For example, the permeable support 440 can be shaped and sized such that the cavity 452 is slightly larger than a head or tip of a penis of a user. The permeable support 440 can include a portion having a curved or convex shape in contact with the permeable membrane 430 such that the permeable membrane 430 is also curved or convex. The permeable support 440 can support the permeable membrane 430 such that the permeable membrane 430 can rest against the skin of the head or tip of the penis with the urethral opening directed toward a bottom surface of the impermeable casing 450, and thus creating a comfortable and at least partially enclosed interface for engagement with the area of the body (e.g., the head and/or neck of a penis of a user) near the urethral opening.

In some implementations, the permeable support 440 can be made of a rigid plastic. In some implementations, the permeable support 440 can have any suitable shape and be formed of any suitable material. For example, the permeable support 440 can be flexible. Additionally, the permeable support 440 can be formed of aluminum, a composite of plastic and aluminum, some other metal and/or a composite of plastic and another metal. In some implementations, the permeable support 440 can be formed of a natural material, such as, for example, plant fibers (e.g., Greener Clean manufactured by 3M®). The natural material can include openings that allow fluid to flow through the natural material. In some embodiments, the permeable support 440 can be formed of perforated coated paper, such as tubular waxed paper.

The permeable support 440 can define one or more openings (e.g., an array of openings) to allow for fluid flow from the permeable membrane 430 to the reservoir 410. In some implementations, the permeable support 440 can include membrane supports (e.g., struts) extending across an opening such that the opening is divided into an array of distinct slot-shaped openings. The membrane supports can be used to support the permeable membrane 430. For example, the membrane supports can maintain the shape of the permeable membrane 430 against the skin of a penis of a user and/or near a urethral opening of a user such that urine flowing from the urethral opening contacts and travels through the permeable membrane 430. In some implementations, the permeable support 440 can define several openings having a variety of shapes, such as a plurality of round openings. In some implementations, the permeable support 440 can be formed of spun plastic (e.g., non-woven permeable nylon and polyester webbing) such that the permeable support 440 can have many openings. In some implementations, the permeable support 440 can be formed of a porous material. For example, the permeable support 440 can be a porous glass container defining frits. In other implementations, the permeable support 440 can define an opening in the permeable support 440 and the opening can be covered by a mesh screen defining many smaller openings. In some embodiments, the reservoir 410 can include any spaces and/or openings defined within the permeable support 440 (e.g., spaces within porous material or defined within spun plastic material).

The reservoir 410 can be any suitable shape and/or have any diameter (or other dimension) suitable for receiving and transporting urine during use of the system 400. In some implementations, the reservoir 410 can be sized such that the reservoir 410 is capable of collecting and temporarily holding a large or small amount of urine until the urine can be removed from the reservoir via the outlet 420. For example, the reservoir 410 can be sized such that the reservoir 410 is configured to hold a small amount of urine as may be released due to incontinence. In some implementations, the reservoir 410 can be sized such that the reservoir 410 is configured to hold a large amount of urine as may be released during voiding of a full bladder. In some implementations, the reservoir 410 can be sized such that the reservoir is configured to collect and hold a small or large amount of urine while the urine is simultaneously removed via, for example, gravity and/or a pump, such as the vacuum source 470. Said another way, the reservoir 410 can function as a sump and be sized such that the reservoir 410 can form a portion of a passageway for urine from the permeable membrane 430, through the permeable support 440, through the reservoir 410, and out of the outlet 420. In a condition where the flow rate of urine into the assembly 402 via the permeable membrane 430 is greater than the flow rate of urine through the discharge line 422, a temporary backup of urine may occur in the reservoir 410. Thus, the reservoir 410 can be sized to contain a volume of fluid that may temporarily accumulate due to the difference in flow rates into and out of the assembly 402.

Although the outlet 420 is shown as extending from the side of the reservoir 410, in some implementations, the outlet 420 can extend from the bottom of the reservoir 410.

The external receptacle 460, via the discharge line 422, can collect fluid exiting the reservoir 410 through the outlet 420. The external receptacle 460 can be a sealed container. In some implementations, the external receptacle 460 can be disposable. In some implementations, the external receptacle 460 can be configured to be sterilized and reused.

In some implementations, gravity can cause fluid within the reservoir 410 to follow a flow path (i.e., the fluid flow path including the outlet 420 and the discharge line 422) from the reservoir 410 to the external receptacle 460. In some implementations, the vacuum source 470 can assist and/or provide the pressure differential needed to draw fluid voided from the urethral opening of a user into the permeable support 440, into the reservoir 410, and from the reservoir 410 into the external receptacle 460. The vacuum source 470 can be fluidically coupled to the external receptacle 460 via a vacuum line 424 such that gaseous fluid is drawn from the external receptacle 460 via the vacuum line 424. As a result of the decrease in pressure within the external receptacle 460 caused by the drawing of gaseous fluid out of the external receptacle 460, liquid and/or gaseous fluid can be drawn from the reservoir 410, through the outlet 420, through the discharge line 422, and into the external receptacle 460. In some implementations, the vacuum source 470 can apply sufficient suction to capture all or substantially all of the urine voided by a user in a variety of positions (e.g., when a male user is lying on his side or back).

The vacuum source 470 can have a sufficiently high vacuum strength and air volume transport rate such that rapid air and liquid aspiration is maintained over a portion of or the entire permeable membrane 430. In some implementations, the one or more openings of the permeable support 440 are distributed over an area that is slightly larger than the area of the permeable membrane 430 that is configured to be wetted by urine flow in operation. Thus, the partial vacuum created by the vacuum source 470 in combination with the one or more openings of the permeable support 440 and the permeable membrane 430 can draw the urine contacting the permeable membrane 430 into the assembly 402 and, specifically, into the reservoir 410. In some implementations, however, the one or more openings of the permeable support 440 should not be distributed over too large of an area of the permeable support 440 because the partial vacuum strength may be reduced, thereby reducing the urine collection rate and the efficiency of the system 400.

In some implementations, the vacuum source 470 can be the same or similar in structure and or function to the vacuum source 170 described above with respect to the system 100 shown in FIG. 1. In some implementations, urine collected by any of the systems and/or assemblies described herein can be sampled for analysis using urine strips similarly as describe above with respect to the system 100 shown in FIG. 1. In some implementations, the external receptacle 460 can be the same or similar in structure and/or function to the external receptacle 160 described above with respect to the system 100 shown in FIG. 1.

Although described as being intended for use by an adult male, in some implementations the system 400 can be used in adult, pediatric, male, female, and veterinary applications for animals of different species and sizes. In female applications, the assembly 402 can be placed between the legs or labia of the user and held snugly against the external urethra by the pressure of friction from the user's body, by the pressure of the legs or by such means as an undergarment, elastic strips, and/or adhesive tape. In male applications, the assembly 402 can be placed such that a penis of a user is disposed within the assembly 402 (e.g., within a cavity formed within the assembly 402). A male user can use the assembly 402 in any suitable position, such as, for example, while lying on his back, lying on his side, sitting, or standing. In some implementations, the head of the penis of the male user can be placed in contact with the permeable membrane 430 during urination. In some implementations, the head of the penis of the male user can be disposed at least partially within the cavity 452, but not placed in contact with the permeable membrane 430 during urination.

Figure 6:
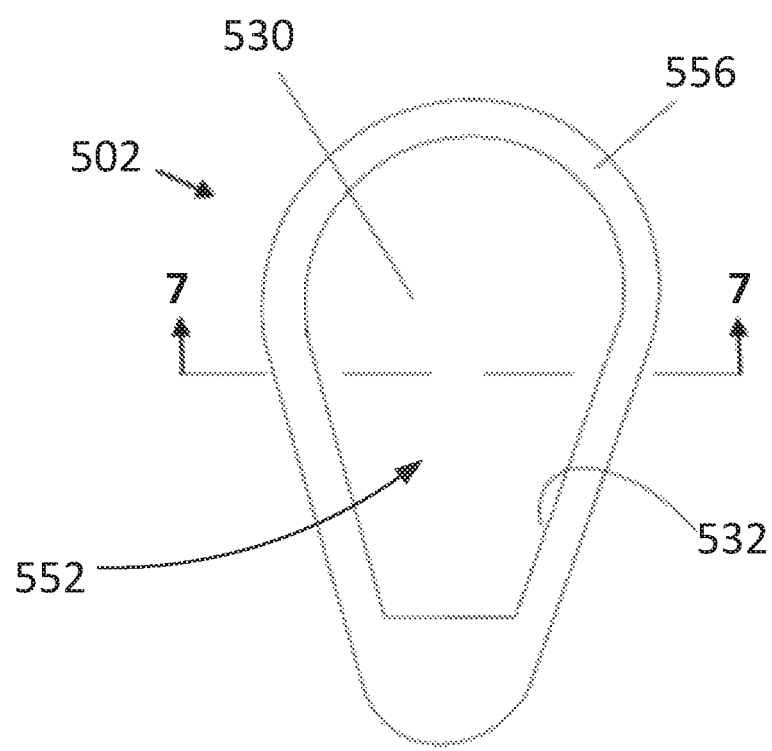
FIG. 6 is a top view of an assembly, according to an embodiment.
Figure 7:
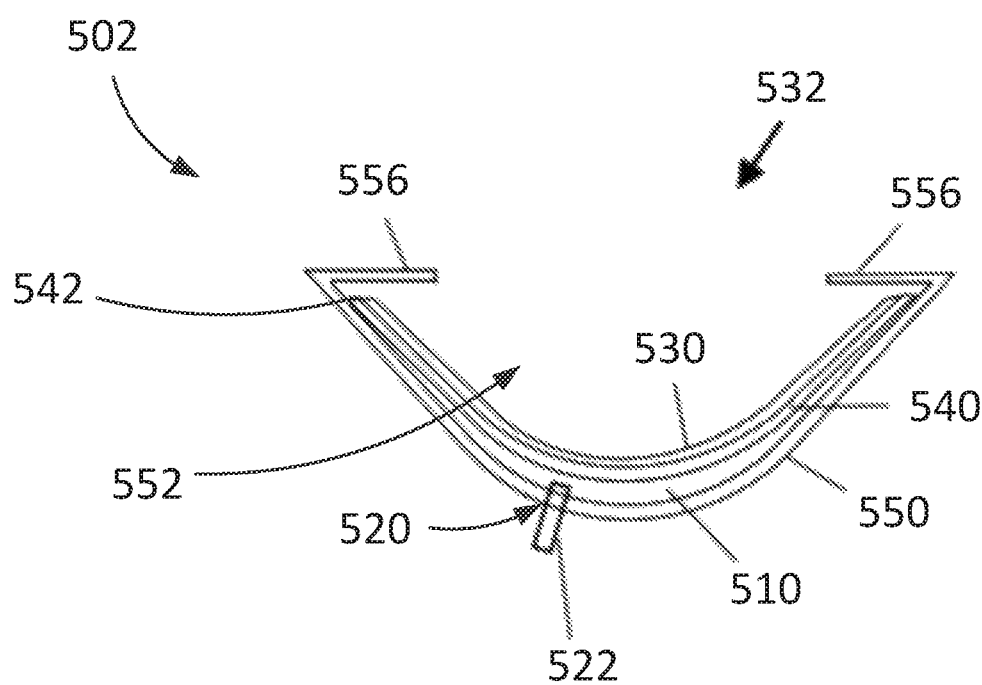
FIG. 7 is a cross-sectional view of the assembly of FIG. 5 taken along line 7-7 of FIG. 5.

FIG. 6 is a top view of an assembly 502. FIG. 7 is a cross-sectional view of the assembly 502 taken along line 7-7 in FIG. 6. The assembly 502 includes a permeable membrane 530, a permeable support 540, and an impermeable casing 250 (also referred to herein as an "impermeable layer"). The permeable membrane 530 and the permeable support 540 are disposed within the impermeable casing 550. The permeable membrane 530, the permeable support 540, and the impermeable casing 550 can be the same or similar in structure and/or function to the permeable membrane 430, the permeable support 440, and the impermeable casing 450 described above with reference to the system 400. For example, the permeable support 540 and the impermeable casing 550 collectively define a reservoir 510 (also referred to herein as a "chamber"). The impermeable casing 550 defines an opening 532. The assembly 502 also includes an outlet 520 (also referred to herein as a "port") in fluidic communication with the reservoir 510.

The permeable support 540 and the permeable membrane 530 can be arranged such that the impermeable membrane 550 and the permeable support 540 and/or the permeable membrane 530 collectively define a cavity 552 within the permeable membrane 530. The impermeable casing 550 can direct fluid toward the reservoir 510 and/or reduce and/or prevent fluid from exiting the assembly 502 except via the outlet 520. In some implementations, the assembly 502 can be arranged such that a fluid can flow through the opening 532, into the cavity 552, through the permeable membrane 530, through the permeable support 540, into the reservoir 510, and out of the outlet 520. In some implementations, the assembly 502 can be arranged such that a user's penis can be inserted through the opening 532 such that the user's urethral opening is disposed within the cavity 552 and a fluid can flow from the user's urethral opening, into the cavity 552, through the permeable membrane 530, through the permeable support 540, into the reservoir 510, and out of the outlet 520. A discharge line 522 (e.g., a tube) (also referred to herein as a "received tube") can extend through the outlet 520. As shown in FIG. 7, a first end of the discharge line 522 can be positioned within the reservoir 510, and the discharge line 522 can extend through the impermeable casing 550 such that fluid in the reservoir 510 can be transported away from the assembly 502 via the discharge line 522. A second end of the discharge line 522 can be fluidically coupled to an external receptacle (e.g., external receptacle 460). The external receptacle can be in fluidic communication with a vacuum source (e.g., vacuum source 470) via a vacuum line (e.g., vacuum line 424). The discharge line 522 and the vacuum line can both include flexible tubing, such as, for example, flexible plastic tubing.

More specifically, the impermeable casing 550 can define an interior region accessible via the opening 532. The permeable membrane 530 and the permeable support 540 can be disposed within the interior region of the impermeable casing 550. The impermeable casing 550 can be any suitable shape. For example, in some implementations, the impermeable casing 550 can be bowl-shaped. As shown in FIG. 7, the impermeable casing 550 can include a curved or concave bottom surface opposite the opening 532. As shown in FIGS. 6 and 7, the impermeable casing 550 can include a lip 556 surrounding the opening 532. The lip 556 can define the opening 532 such that the opening 532 is opposite the bottom surface of the impermeable casing 550 and the interior region of the impermeable casing 550 is bounded (and collectively defined) by the curved or concave bottom surface of the impermeable casing 550, the lip 556, and the opening 532. The lip 556 can be shaped and sized such that the lip 556 can reduce the potential of urine flowing out of the opening 532 and/or such that the risk of splashing of urine through the opening 532 is reduced. In some implementations, the opening 532 has a width and/or length similar in size to the diameter of a user's penis. In some implementations, the opening 532 is larger in width and/or length than the diameter than a user's penis. In some implementations, the opening 532 can be irregularly shaped. For example, as shown in FIG. 6, the opening 532 (and the impermeable casing 550) can have a rounded or semi-circular first portion and a second portion that tapers from a first side adjacent to the first portion having a first width to a second width smaller than the first width.

As shown in FIG. 7, the permeable support 540 can have a bottom side with a periphery 542. The periphery 542 can be secured (via, e.g., adhesive) to an inner wall of the impermeable casing 550. In some implementations, the periphery 542 can be secured at one or more locations (or continuously along the periphery) such that the reservoir 510 formed by the permeable support 540 and the impermeable casing 550 is a suitable size for collecting and/or transporting urine, and such that the cavity 552 is sufficiently sized for a portion or all of a user's penis to be disposed within the cavity 552. In some implementations, the impermeable casing 550 can be attached to the permeable support 540 via any suitable retention mechanism, such as, for example, retainer clips or other fasteners. In some implementations, the permeable support 540 and the permeable membrane 530 can be placed within the impermeable casing without additional coupling mechanisms.

The impermeable layer 550 can be impermeable to fluid, such as, for example, urine. In some implementations, the impermeable layer 550 can have a fluid transportation function and can assist in directing fluid towards the reservoir 510 and/or through the outlet 520 of the reservoir 510. In some implementations, the impermeable layer 550 can be formed as an integral, unitary structure. In other implementations, the impermeable layer 550 can be a multi-piece structure. The impermeable layer 550 can be a pre-molded (e.g., injection or blow molded) component. Alternatively, the impermeable layer 550 can be formed of a material, such as elongate strips of an adhesive tape, wrapped around at least a portion of the reservoir 510, a portion of the permeable support 540, and/or a portion of the permeable membrane 530. In some embodiments, the impermeable layer 550 can be formed of cardboard, pressed paper, and/or coated paper. In some embodiments, the impermeable layer 550 can be flexible.

The permeable membrane 530 can be formed of a material that has permeable properties with respect to liquids such as urine. The permeable properties can be wicking, capillary action, diffusion, or other similar properties or processes, and are referred to herein as "permeable" and/or "wicking." The permeable membrane 530 can have a high absorptive rate and a high permeation rate such that urine can be rapidly absorbed by the permeable membrane 530 and/or transported through the permeable membrane 530. In some implementations, the permeable membrane 530 can be flexible. In some implementations, the permeable membrane 530 can be a ribbed knit fabric. In some implementations, the permeable membrane 530 can include and/or have the moisture-wicking characteristic of gauze, felt, terrycloth, thick tissue paper, and/or a paper towel. In some implementations, the permeable membrane 530 can be soft and/or minimally abrasive such that the permeable membrane 530 does not irritate the skin of the user. The permeable membrane 530 can be configured to wick fluid away from the urethral opening and/or the skin of the user such that the dampness of the skin of the user is lessened and infections are prevented. Additionally, the wicking properties of the permeable membrane 530 can help prevent urine from leaking or flowing beyond the assembly (e.g., out of opening 532) onto, for example, a bed. In some implementations, the permeable membrane 530 can be formed of fine denier polyester fibers coated with a thermoplastic water-based binder system. The tensile with the Webb direction can be, for example, about 45 lbs/inch$^2$ measured using an Instron test method. The weight per permeable membrane can be, for example, about 12 grams measured using the Mettle Gram Scale. The thickness per ten permeable membrane can be, for example, about 2.5", measured using the Gustin-Bacon/Measure-Matic.

The permeable support 540 can be positioned relative to the permeable membrane 530 such that the permeable support 540 maintains the permeable membrane 530 in a particular shape and allows for fluid, such as, for example, urine, to flow through the permeable membrane 530, through the permeable support 540, and into the reservoir 510. In some implementations, the permeable membrane 530 can be disposed on a first, upper side of the permeable support 540, and the second, bottom side of the permeable support 540 can define a boundary of the reservoir 510. As shown in FIG. 7, the permeable support 540 can have a concave shape such that, when the permeable membrane 530 is disposed on the permeable support 540 and the permeable membrane 530 and the permeable support 540 are disposed within the impermeable casing 550, the cavity 552 has a concave bottom. When the permeable support 540 and the permeable membrane 530 are disposed within the impermeable casing 550, the cavity 552 can be aligned with the opening 532 of the impermeable casing 550. The reservoir 510 can be defined by the permeable support 540 and the impermeable casing 550 such that the reservoir 510 is concave and has any suitable shape and/or dimensions.

In some implementations, the permeable support 540 and/or the permeable membrane 530 can be any suitable shape and/or size. In some implementations, the permeable support 540 and the permeable membrane 530 can have the same or similar shape and dimensions. In some implementations, the permeable support 540 and/or the permeable membrane 530 can be shaped such that the outer perimeter of the permeable support 540 and/or the permeable membrane 530 can be the same or similar to the outer perimeter of the top of the impermeable casing 550 and/or the opening 532. In some implementations, the dimensions of the permeable support 540 and/or the permeable membrane 530 can be sized such that the cavity 552 can receive a penis of a user such that a head of the penis can be partially or fully disposed within the cavity 552 (i.e., the shaft of the penis can be disposed within the opening 532 and the head of the penis can be fully disposed within the cavity 552, or the urethral opening of the head of the penis can be disposed within the cavity 552 and the head can be partially disposed within the cavity 552 and partially outside the cavity 552, with the opening 532 surrounding a portion of the head). In some implementations, the cavity 552 can be dimensioned to receive a head of a penis of a user such that urine can be received from the urethral opening of the penis within the cavity 552, by the permeable membrane 530, and/or by the permeable support 540 without urine splashing out of the opening 532.

In some implementations, the permeable support 540 can be configured to maintain the permeable membrane 530 against the skin of a penis of a user and/or near a urethral opening of a user. For example, the permeable support 540 can be shaped and sized such that the cavity 552 is slightly larger than a head or tip of a penis of a user. The permeable support 540 can include a portion having a curved or convex shape in contact with the permeable membrane 530 such that the permeable membrane 530 is also curved or convex. The permeable support 540 can support the permeable membrane 530 such that the permeable membrane 530 can rest against the skin of the head or tip of the penis with the urethral opening directed toward a bottom surface of the impermeable casing 550, and thus creating a comfortable and at least partially enclosed interface for engagement with the area of the body (e.g., the head and/or neck of a penis of a user) near the urethral opening.

In some implementations, the permeable support 540 can be made of a rigid plastic. In some implementations, the permeable support 540 can have any suitable shape and be formed of any suitable material. For example, the permeable support 540 can be flexible. Additionally, the permeable support 540 can be formed of aluminum, a composite of plastic and aluminum, some other metal and/or a composite of plastic and another metal. In some implementations, the permeable support 540 can be formed of a natural material, such as, for example, plant fibers (e.g., Greener Clean manufactured by 3M®). The natural material can include openings that allow fluid to flow through the natural material. In some embodiments, the permeable support 540 can be formed of perforated coated paper, such as tubular waxed paper.

The permeable support 540 can define one or more openings (e.g., an array of openings) to allow for fluid flow from the permeable membrane 530 to the reservoir 510. In some implementations, the permeable support 540 can include membrane supports (e.g., struts) extending across an opening such that the opening is divided into an array of distinct slot-shaped openings. The membrane supports can be used to support the permeable membrane 530. For example, the membrane supports can maintain the shape of the permeable membrane 530 against the skin of a penis of a user and/or near a urethral opening of a user such that urine flowing from the urethral opening contacts and travels through the permeable membrane 530. In some implementations, the permeable support 540 can define several openings having a variety of shapes, such as a plurality of round openings. In some implementations, the permeable support 540 can be formed of spun plastic (e.g., non-woven permeable nylon and polyester webbing) such that the permeable support 540 can have many openings. In some implementations, the permeable support 540 can be formed of a porous material. For example, the permeable support 540 can be a porous glass container defining frits. In other implementations, the permeable support 540 can define an opening in the permeable support 540 and the opening can be covered by a mesh screen defining many smaller openings. In some embodiments, the reservoir 510 can include any spaces and/or openings defined within the permeable support 540 (e.g., spaces within porous material or defined within spun plastic material).

The reservoir 510 can be any suitable shape and/or have any diameter (or other dimension) suitable for receiving and transporting urine during use of a system including assembly 502. In some implementations, the reservoir 510 can be sized such that the reservoir 510 is capable of collecting and temporarily holding a large or small amount of urine until the urine can be removed from the reservoir via the outlet 520. For example, the reservoir 510 can be sized such that the reservoir 510 is configured to hold a small amount of urine as may be released due to incontinence. In some implementations, the reservoir 510 can be sized such that the reservoir 510 is configured to hold a large amount of urine as may be released during voiding of a full bladder. In some implementations, the reservoir 510 can be sized such that the reservoir is configured to collect and hold a small or large amount of urine while the urine is simultaneously removed via, for example, gravity and/or a pump, such as the vacuum source 570. Said another way, the reservoir 510 can function as a sump and be sized such that the reservoir 510 can form a portion of a passageway for urine from the permeable membrane 530, through the permeable support 540, through the reservoir 510, and out of the outlet 520. In a condition where the flow rate of urine into the assembly 502 via the permeable membrane 530 is greater than the flow rate of urine through the discharge line 522, a temporary backup of urine may occur in the reservoir 510. Thus, the reservoir 510 can be sized to contain a volume of fluid that may temporarily accumulate due to the difference in flow rates into and out of the assembly 502.

FIG. 8 is a flowchart illustrating a method of using an assembly to collect urine from a user, according to an embodiment. The method 600 optionally includes, at 602, fluidically coupling a discharge end of a tube of a urine collecting apparatus to a fluid receptacle. The method 600 optionally further includes, at 604, fluidically coupling the discharge end of the tube of the urine collecting apparatus to a source of vacuum.

The method 600 further includes, at 606, disposing the urine collecting apparatus in operative relationship with the urethral opening of the user, with a head of a penis of a male user (e.g. human or animal) disposed through an opening and into a cavity defined by a fluid permeable membrane and a casing of the urine collecting apparatus. The urine collecting apparatus can be the same or similar in structure and/or function to any of the urine collecting apparatus described herein, such as, for example, the assembly 402 in FIG. 5 and/or the assembly 502 in FIGS. 6 and 7. For example, the urine collecting apparatus can include a fluid impermeable casing, a fluid permeable support, a fluid permeable membrane, and a tube. The fluid impermeable casing can define an opening, an interior region, and a fluid outlet. The fluid permeable support can have a first side and a second side. The second side of the fluid permeable support and the fluid impermeable casing can collectively define a reservoir. The fluid permeable support can also be disposed within the interior region of the fluid impermeable casing. The fluid permeable membrane can be disposed on the first side of the support and cover at least a portion of the support. The fluid permeable membrane and the casing can collectively define the cavity. The tube can have a first end disposed in the elongated reservoir and extend through the fluid outlet to a second, fluid discharge end. The assembly can be arranged such that a fluid can flow into the cavity from the urethral opening of the user's penis, flow through the fluid permeable membrane and the fluid permeable support, collect in the reservoir, and flow out of the outlet.

The method 600 also includes, at 608, allowing urine discharged from the penis to be received into the cavity, through the membrane, through the support, and into the reservoir.

The method 600 also includes, at 610, allowing the received urine to be withdrawn from the reservoir via the tube and out of the fluid discharge end of the tube.

The method 600 optionally includes, at 612, allowing the withdrawn urine to be collected in the fluid receptacle.

The method 600 optionally includes, at 614, removing the urine collecting apparatus from the penis of the user. Thus, the urine collecting apparatus can capture and transport urine from a user without having to attach a catheter to the urethral opening of the user's penis. In some implementations, the urine can flow against gravity during collection.

Finally, the method 600 optionally includes, at 616, disposing a second urine collecting apparatus in operative relationship with the urethral opening of the user, with the head of the penis of the user disposed through the opening and into the cavity of the urine collecting apparatus.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A urinary device assembly, comprising:
    a first assembly including:
        a first layer having a guide that at least partially extends about an opening disposed through a portion of the first layer;
        at least one second layer disposed in at least partial contact with the first layer; and
        a collector separate from and disposed between the first layer and the second layer in at least partial alignment with the opening, the collector at least partially defining an aperture and a completely enclosed channel in fluid communication with the opening and configured to receive fluid through the opening, wherein the channel includes an enclosed chamber within the collector and at least one of the channel or the collector form a circular or ovular ring; and
    a tube secured to the collector and in fluid communication with the aperture in the collector to direct the fluid away from the collector.

2. The urinary device assembly of claim 1, wherein the guide includes a generally convex outer surface.

3. The urinary device assembly of claim 1, wherein at least a portion of the guide is arced around the opening.

4. The urinary device assembly of claim 1, wherein the first assembly is sized and dimensioned to be disposed between at least one of legs or labia of a female user over a urethral opening of the female user.

5. The urinary device assembly of claim 4, wherein the opening is positioned on the first assembly to receive urine discharged from the urethral opening of the female user.

6. The urinary device assembly of claim 1, wherein the tube includes a first end in fluid communication with the channel.

7. The urinary device assembly of claim 1, wherein the collector in at least partial alignment with the opening at least partially overlaps with the opening.

8. A urinary device assembly, comprising:
    a first assembly sized and dimensioned to be positioned between the legs of a female user over a urethral opening of the female user, the first assembly including:
        a first layer having a guide that at least partially extends about an opening disposed through a portion of the first layer;
        a second layer disposed in at least partial engagement with the first layer; and
        a collector separate from and disposed at least partially between the first layer and the second layer in at least partial alignment with the opening, the collector at least partially defining an aperture and a completely enclosed channel in fluid communication with the opening and configured to receive fluid through the opening, wherein the collector forms a circular or ovular ring; and
    a tube secured to the collector and in fluid communication with the aperture to direct fluid away from the collector.

9. The urinary device assembly of claim 8, wherein the guide includes a generally convex outer surface.

10. The urinary device assembly of claim 8, wherein at least a portion of the guide is arced around the opening.

11. The urinary device assembly of claim 8, wherein the tube includes a first end in fluid communication with the channel of the collector.

12. The urinary device assembly of claim 8, wherein the collector in at least partial alignment with the opening at least partially overlaps with the opening.

13. The urinary device assembly of claim 8, further comprising:
    a fluid permeable layer disposed along a portion of the first layer over at least a portion of the opening; and
    a fabric layer that extends over the fluid permeable layer with the fluid permeable layer disposed between at least a portion of the first assembly and the fabric layer.

14. A method of collecting urine from a female user, the method including:
    disposing a urine collecting assembly in operative relationship with a urethral opening of the female user with urine collecting assembly between legs of the female user;
    receiving urine discharged from the urethral opening through an opening in a first layer of the urine collecting assembly and into a completely enclosed channel at least partially defined by a collector of the urine collecting assembly, the collector including a circular or ovular ring having an aperture; and
    withdrawing the urine from the channel through the aperture in the circular or ovular ring via a tube secured to the collector.

15. The method of claim 14, further comprising:
    fluidically coupling a fluid discharge end of the tube to a fluid receptacle;
    fluidically coupling the fluid discharge end of the tube to a source of vacuum to assist in withdrawing urine via the tube from a reservoir of the urine collecting apparatus; and
    collecting the urine withdrawn from the reservoir in the fluid receptacle.

16. The method of claim 14, further comprising guiding the urine to the channel with a guide on the first layer that is arced around the opening of the first layer.

17. The method of claim 14, further comprising securing the urine collecting assembly against the urethral opening of the female user with an undergarment worn by the female user.

* * * * *